United States Patent [19]
Pamukcu et al.

[11] Patent Number: 6,156,528
[45] Date of Patent: *Dec. 5, 2000

[54] METHODS FOR USING A PHOSPHODIESTERASE IN PHARMACEUTICAL SCREENING TO IDENTIFY COMPOUNDS FOR TREATMENT OF NEOPLASIA

[75] Inventors: Rifat Pamukcu, Spring House; Gary A. Piazza, Doylestown, both of Pa.

[73] Assignee: Cell Pathways, Inc, Horsham, Pa.

[*] Notice: This patent issued on a continued prosecution application filed under 37 CFR 1.53(d), and is subject to the twenty year patent term provisions of 35 U.S.C. 154(a)(2).

This patent is subject to a terminal disclaimer.

[21] Appl. No.: 09/216,070

[22] Filed: Dec. 19, 1998

Related U.S. Application Data

[63] Continuation of application No. 08/866,027, May 30, 1997, Pat. No. 5,858,694.

[51] Int. Cl.[7] .................................................. C12Q 1/26
[52] U.S. Cl. ................................ 435/25; 435/13; 435/19; 435/184
[58] Field of Search ............................... 435/4, 6, 15, 19, 435/25, 184, 196; 424/9.1, 9.2; 436/64

[56] References Cited

U.S. PATENT DOCUMENTS

| | | |
|---|---|---|
| 3,031,450 | 4/1962 | Fischer et al. . |
| 3,161,654 | 12/1964 | Shen . |
| 3,322,755 | 5/1967 | Roch et al. . |
| 3,517,005 | 6/1970 | Cronin et al. . |
| 3,594,480 | 7/1971 | Cronin et al. . |
| 3,647,858 | 3/1972 | Hinkley et al. . |
| 3,654,349 | 4/1972 | Shen et al. . |
| 3,780,040 | 12/1973 | Schnettler et al. . |
| 3,812,127 | 5/1974 | Cronin et al. . |
| 3,819,631 | 6/1974 | Broughton et al. . |
| 3,865,840 | 2/1975 | Carson . |
| 3,920,636 | 11/1975 | Takahasi et al. . |
| 4,001,237 | 1/1977 | Partyka et al. . |
| 4,001,238 | 1/1977 | Partyka et al. . |
| 4,039,544 | 8/1977 | Broughton et al. . |
| 4,060,615 | 11/1977 | Matier et al. . |
| 4,076,711 | 2/1978 | Ganguly et al. . |
| 4,079,057 | 3/1978 | Juby et al. . |
| 4,098,788 | 7/1978 | Crenshaw et al. . |
| 4,101,548 | 7/1978 | Crenshaw et al. . |
| 4,102,885 | 7/1978 | Crenshaw et al. . |
| 4,138,561 | 2/1979 | Crenshaw et al. . |
| 4,146,718 | 3/1979 | Jenks et al. . |
| 4,161,595 | 7/1979 | Kaplan et al. . |
| 4,171,363 | 10/1979 | Crenshaw et al. . |
| 4,208,521 | 6/1980 | Crenshaw et al. . |
| 4,209,623 | 6/1980 | Juby . |
| 4,423,075 | 12/1983 | Dvornik et al. . |
| 4,457,927 | 7/1984 | Biere et al. . |
| 4,460,590 | 7/1984 | Möller . |
| 4,460,591 | 7/1984 | DeGraw et al. . |
| 4,837,239 | 6/1989 | Benjamin et al. . |
| 4,880,810 | 11/1989 | Lowe, III et al. . |
| 4,885,301 | 12/1989 | Coates . |
| 4,923,874 | 5/1990 | McMahon et al. . |
| 4,971,972 | 11/1990 | Doll et al. . |
| 5,073,559 | 12/1991 | Coates . |
| 5,091,431 | 2/1992 | Tulshian et al. . |
| 5,147,875 | 9/1992 | Coates et al. . |
| 5,175,151 | 12/1992 | Afonso et al. . |
| 5,223,501 | 6/1993 | Chakravarty et al. . |

(List continued on next page.)

FOREIGN PATENT DOCUMENTS

| | | |
|---|---|---|
| 0 330 004 A1 | 6/1989 | European Pat. Off. . |
| 0 347 146 A2 | 12/1989 | European Pat. Off. . |
| 0 349239 A2 | 1/1990 | European Pat. Off. . |
| 0 351058 | 1/1990 | European Pat. Off. . |
| 0 352960 A2 | 1/1990 | European Pat. Off. . |
| 0 395328 A2 | 10/1990 | European Pat. Off. . |
| 0 428268 A2 | 5/1991 | European Pat. Off. . |
| 0 463756 A1 | 1/1992 | European Pat. Off. . |
| 0 485157 A2 | 5/1992 | European Pat. Off. . |
| 0 485158 A2 | 5/1992 | European Pat. Off. . |
| 0 485171 A2 | 5/1992 | European Pat. Off. . |
| 0 485172 A2 | 5/1992 | European Pat. Off. . |
| 0 485173 A2 | 5/1992 | European Pat. Off. . |
| 0 508586 A1 | 10/1992 | European Pat. Off. . |
| 0 526004 A1 | 2/1993 | European Pat. Off. . |
| 0 607439 A1 | 7/1994 | European Pat. Off. . |
| 0 743304 A1 | 5/1996 | European Pat. Off. . |
| 0 722937 A1 | 7/1996 | European Pat. Off. . |
| 3038166 | 5/1981 | Germany . |
| 274218 | 12/1989 | Germany . |
| 56-53659 | 5/1981 | Japan . |
| 57-167974 | 10/1982 | Japan . |
| 8-311035 | 11/1996 | Japan . |
| 807826 | 1/1959 | United Kingdom . |
| 2063249 | 6/1981 | United Kingdom . |
| WO 92/03419 | 3/1992 | WIPO . |
| WO 93/07149 | 4/1993 | WIPO . |
| WO 93/12095 | 6/1993 | WIPO . |
| WO 94/05661 | 3/1994 | WIPO . |

(List continued on next page.)

OTHER PUBLICATIONS

Earnest D. Piroxicam and Other cyclooxygenase Inhibitors: Potential for Cancer Chemoprevention. J of Cellular Biochemistry Supplement 161:156–166, 1992.

(List continued on next page.)

*Primary Examiner*—Ralph Gitomer
*Attorney, Agent, or Firm*—Robert W. Stevenson

[57] ABSTRACT

This invention provides a method to identify compounds potentially useful for the treatment of neoplasia in mammals. The phosphodiesterase inhibitory activity of a compound is determined along with COX inhibitory activity. Growth inhibitory and apoptosis inducing effects on cultured tumor cells are also determined. Compounds that exhibit phosphodiesterase inhibiton, growth inhibition and apoptosis induction, but not substantial prostaglandin inhibitory activity, are desirable for the treatment of neoplasia.

14 Claims, 13 Drawing Sheets

U.S. PATENT DOCUMENTS

| | | |
|---|---|---|
| 5,239,083 | 8/1993 | Kumazawa et al. . |
| 5,250,535 | 10/1993 | Verheyden et al. . |
| 5,254,571 | 10/1993 | Coates et al. . |
| 5,358,952 | 10/1994 | Moschel et al. . |
| 5,376,683 | 12/1994 | Klar et al. . |
| 5,393,755 | 2/1995 | Neustadt et al. . |
| 5,401,774 | 3/1995 | Pamukcu et al. . |
| 5,439,895 | 8/1995 | Lee et al. . |
| 5,464,861 | 11/1995 | Dobrusin et al. . |
| 5,488,055 | 1/1996 | Kumar et al. . |
| 5,614,530 | 3/1997 | Kumar et al. . |
| 5,614,627 | 3/1997 | Takase et al. . |
| 5,674,876 | 10/1997 | Gilbert et al. . |
| 5,696,159 | 12/1997 | Gross et al. . |
| 5,728,563 | 3/1998 | Tanaka . |
| 5,731,167 | 3/1998 | Stracke et al. . |
| 5,756,818 | 5/1998 | Buchmann et al. . |
| 5,798,246 | 8/1998 | Au-Young et al. . |
| 5,798,373 | 8/1998 | Warrellow . |
| 5,849,770 | 12/1998 | Head et al. . |
| 5,852,035 | 12/1998 | Pamukcu et al. . |
| 5,858,694 | 1/1999 | Piazza et al. .............................. 435/19 |
| 5,869,519 | 9/1999 | Karanewsky et al. . |
| 5,874,440 | 2/1999 | Pamukcu et al. . |
| 5,891,896 | 4/1999 | Warrellow et al. . |
| 5,922,595 | 7/1999 | Fisher et al. . |
| 5,932,423 | 8/1999 | Au-Young et al. . |
| 5,932,465 | 8/1999 | Loughney . |
| 5,942,520 | 8/1999 | Pamukcu et al. . |
| 5,948,779 | 9/1999 | Sperl et al. . |
| 6,015,677 | 1/2000 | Beavo et al. ............................... 435/6 |

FOREIGN PATENT DOCUMENTS

| | | |
|---|---|---|
| WO 94/19351 | 9/1994 | WIPO . |
| WO 94/29277 | 12/1994 | WIPO . |
| WO 95 18969 | 7/1995 | WIPO . |
| WO 95/26743 | 10/1995 | WIPO . |
| WO 97/03070 | 1/1997 | WIPO . |
| WO 97/03985 | 2/1997 | WIPO . |
| WO 97/24334 | 7/1997 | WIPO . |
| WO 98/14448 | 4/1998 | WIPO . |
| WO 98/15530 | 4/1998 | WIPO . |
| WO 98/16224 | 4/1998 | WIPO . |
| WO 98/16521 | 4/1998 | WIPO . |
| WO 98/17668 | 4/1998 | WIPO . |
| WO 98/08848 | 5/1998 | WIPO . |
| WO 98/23597 | 6/1998 | WIPO . |
| WO 98/38168 | 9/1998 | WIPO . |
| WO 96/32379 | 10/1998 | WIPO . |

OTHER PUBLICATIONS

Jiang X. Inhibition of Calmodulin–Dependent Phosphodiesterase Induces Apoptosis in Human Leukemic Cells. Proc Natl Acad Sci USA 93:11236–41, Oct. 1996.

Ahlstrom, M.; Lamberg–Allardt, C., Regulation of adenosine 3',5'–cyclic monophosphate (cAMP) accumulation in UMR–106 osteoblastlike cells: role of cAMP–phosphodiesterase and cAMP efflux, Biochem. Pharmacol. (1999), 58(8), 1335–1340.

Ahn, H.S. et al., Effects of Selective Inhibitors on Cyclic Nucleotide Phosphodiesterases of Rabbit Aorta, Biochemical Pharmacology, vol. 38, No. 19, pp. 3331–3339 (1989).

Ahn, Ho–Sam et al., Potent Tetracyclic Guanine Inhibitors of PDE1 and PDE5 Cyclic Guanosine Monophosphate Phosphodiesterases with Oral Antihypertensive Activity; J. Med. Chem. 1997, 40, pp. 2196–2210.

Altiok N. et al., Bradykinin inhibition of cyclic AMP accumulation in D384 astrocytoma cells. Evidence against a role of cyclic GMP, Neurochem Int. 1992 Sep.; 21(2):209–13.

Anderson, Thomas L. G. et al., Interactions between isoprenaline, sodium nitroprusside, and isozyme–selective phosphodiesterase inhibitors on ADP–induced aggregation and cyclic Nucleotide levels in human platelets (Abstract Only), J. Cardiovasc. Pharmacol. 18(2) pp. 237–242 (1991).

Antonenko S.G. et al., [The role of the components of the cyclic nucleotide system in N–nitrosodiethylamine–induced hepatic carcinogenesis in rats] (Article in Russian), Eksp. Onkol. 1990;12(5):18–21.

Badrieh, Y., et al., Chem. Ber., vol. 125, pp. 667–674 (1992).

Barnett, Mary S. et al., Initial biochemical and functional characterization of cyclic nucleotide phosphodiesterase isozymes in canine colonic smooth muscle (Abstract Only), J. Pharmacol. Exp. Ther., 264(2) pp. 801–812 (1993).

Belousova, A. K. et al., Role of cyclic nucleotides in tumor growth regulation, (Article written in Russian) Vestn. Akad. Med, Nauk SSSR (1980), (6), 86–9.

Beltman, Jerlyn et al., Characterization of cyclic nucleotide phosphodiesterases with cyclic GMP analogs: topology of the catalytic domains, Mol. Pharmacol. (1995), 47(2), 330–9.

Bergstrand, Hakan et al., Effects of Antiallergic Agents, Compound 48/80, and Some Reference Inhibitors on the Activity of Partially Purified Human Lung Tissue Adenosine Cyclic 3',5'–Monophosphate and Guanosine Cyclic 3',5'–Monophosphate Phosphodiesterases, Molecular Pharmacology, 13, pp. 38–43 (1976).

Biddle, William et al., Antineoplastic Effect of the Pyrimido–Pyrimidine Derivative: RA 233, Pathologie Biologie, Jan., 1984, pp. 9–13.

Bjarnason et al., Gastroenterology, vol. 94, No. 4, pp. 1070–1074 (1988).

Blaya, C. et al., Effect of the protein kinase inhibitors, 1–(5–isoquinolinylsulfonyl)–2–methylpiperazine H–7 and N–(2–[methylamino]ethyl)–5–isoquinoline–sulfonamide H–8 on Lewis lung carcinoma tumor progression, European Journal of Pharmacology, 354, pp. 99–104 (1998).

Brogden, R.N. et al., Drugs, vol. 16, pp. 97–114 (1978).

Broughton, B.J. et al., Antiallergic Activity of 2–Phenyl–8–azapruin–6–ones, Journal of Medicinal Chemistry, vol. 18, No. 11, pp. 1117–1118 (1975).

Butt, Elke et al., Characterization of cyclic nucleotide phosphodiesterases with cyclic MAP analogs: topology of the catalytic sites and comparison with other cyclic AMP–binding proteins, Mol. Pharmacol. (1995), 47(2), 340–7.

Carter et al., Chemotherapy of Cancer, $2^{nd}$ Ed., John Wiley & Sons, NY, NY, 1981, pp. 362–365.

Chang, W. et al., Sulindac Sulfone Modulates the Expression and Cellular Localization of b–Catenin in Human Colon Carcinoma Cells, Digestive Disease Week, Apr. 1, 1999.

Clarke, W.R. et al., The type III phosphodiesterase inhibitor milrinone and type V PDE inhibitor dipyridamole individually and synergistically reduce elevated pulmonary vascular resistance (Abstract Only), Pulm. Pharmacol., 7(2), pp. 81–89, (1994).

Cohan, V.L. et al., In vitro pharmacology of the novel phosphodiesterase type 4 inhibitor, CP–80633, J. Pharmacol. Exp. Ther. (1996), 278(3), 1356–1361.

Cohen L.A. et al., Cyclic nucleotide phosphodiesterase activity in normal and neoplastic rat mammary cells grown in monolayer culture, Cancer Res. 1976 Jun.;36(6):2007–12.

Cote, Mylene, et al., Comparative involvement of cyclic nucleotide phosphodiesterases and adenylyl cyclase on adrenocorticotropin–induced increase of cyclic adenosine monophosphate in rat and human glomerulose cells, Endocrinology (1999), 140(8), 3594–3601.

Curtis–Prior, P.B. et al., Cyclic Nucleotide Phosphodiesterase Activity of Human Normal and Carcinomatous Lung Tissue, The Lancet, pp. 1224–1225 Dec. 4, 1976.

Delporte C. et al., Role of phosphodiesterase II in cross talk between cGMP and cAMP in human neuroblastoma NB–OK–1 cells, Am. J. Physiol. 1996 Jan.;270(1 pt 1):C286–92.

Dickinson, Natalie T. et al., Activation of cGMP–stimulated phosphodiesterase by nitroprusside limits cAMP accumulation in human platelets: effects on platelet aggregation, Biochem. J. (1997), 323(2), 371–377.

Drees, Markus et al., 3',5'–Cyclic Nucleotide Phosphodiesterase in Tumor Cells as Potential Target for Tumor Growth Inhibition, Cancer Research 53, pp. 3058–3061 (1993).

Duarte, Juan et al., Effects of visnagin on cyclic nucleotide phosphodiesterases and their role in its inhibitory effects on vascular smooth muscle contraction, Gen. Pharmacol. (1998), vol. Date 1999, 32(1), 71–74.

Duggan, D.E. et al., Clin. Pharm. & Therapeutics, vol. 21, No. 3, pp. 326–335 (1976).

Duggan, D.E. et al., J. Pharm. & Exper. Therap., vol. 201, No. 1, pp. 8–13 (1977).

Easwaran, V. et al., The Ubiquitin–Proteasome Pathway and Serine Kinase Activity Modulate Adenomatous Polyposis Coli Protein–mediated Regulation of β–Catenin–Lymphocyte Enhancer–binding Factor Signaling, The Journal of Biological Chemistry, vol. 274, No. 23, pp. 16641–16645, Jun. 4, 1999.

Eckly–Michel, Anita E. et al., Chelerythrine, a protein kinase C inhibitor, interacts with cyclic nucleotide phosphodiesterases, Eur. J. Pharmacol. (1997), 324(1), 85–88.

Emami S. et al., Histamine and VIP interactions with receptor–cyclic AMP systems in the human gastric cancer cell line HGT–1, Life Sci. 1983 Aug. 1;33(5):415–23.

Epstein, P.M. et al. Increased Cyclic Nucleotide Phospho Di Esterase Activity Associated with Proliferation and Cancer in Human Murine Lymphoid Cells. Dep. Pharmacol., Univ. Tex. Med. Sch., M.D. Anderson Hospital, Houston, Tex. 77030, USA. BIOSIS: 78:140912 Abstract No Date Given. Federation Proceedings (1972) of the Federation of American Societies for Experimental Biology abstract Nos. 2044 and 2045.

Ferreira, S.H. et al., The molecular mechanism of action of peripheral morphone analgesia: stimulation of the cGMP system via nitric oxide release, European Journal of Pharmacology, 201 pp. 121–122 (1991).

Fischmeister, Rodolphe, et al., Cardiac calcium current regulation by the cGMP/NO pathway, C.R. Seances Soc. Biol. Ses Fil. (1996), 190(2–3), 181–206.

Folbergrova J. et al., Cyclic AMP levels of C6 glioma cells treated with cisdichlorodiammine platinum (cis–DDP), Neoplasma 1987;34(1):3–13.

Frattola L. et al., Characteristics of the cyclic AMP–phosphodiesterase activator in human brain tumours, J. Neurol. Sci. 1981 Nov.–Dec.;52(2–3):269–77.

Gaffen, J. D. et al.: Increased killing of malignant cells by giving indomethacin with methotrexate, p. 30; column 1; XP002084860Chemical Abstract, vol. 106, No. 11, Mar. 16, 1987, abstract No. 78377, J.D.

Gallo–Payet, Nicole et al., Cyclic AMP–independent effects of ACTH on glomerulosa cells of the rat adrenal cortex, J. Steroid Biochem. Mol. Biol. (1999), 69(1–6), 335–342.

Gilman, S.C. et al., Nonsteroidal Anti–inflammatory Drugs in Cancer Therapy, (circa 1985).

Giorgi M. et al., Induction of cyclic AMP and cyclic 3':5'–cyclic nucleotide phosphodiesterase activities in neuroblastoma lines under differentiating conditions, Int. J. Dev. Neurosci. 1997 Jun.;15(3):309–19.

Giorgi, Mauro et al., Characterization of 3':5' cyclic nucleotide phosphodiesterase activities of mouse neuroblastoma N18TG2 cells, FEBS Lett. 324(1) pp. 76–80 (1993).

Glavin, G.B. et al., Toxicology and Applied Pharmacology, vol. 83, pp. 386–389 (1986).

Gonzaga, R.A.F. et al., The Lancet, Mar. 30, 1985, p. 751.

Hagiwara, Masatoshi et al., Effect of 1–(3–chloroanilino)–4–phenylpthalazine (MY–5445), a specific inhibitor of cyclic CMP phosphodiesterase, on human platelet aggregation (Abstract Only), J. Pharmacol. Exp. Ther. 229(2) pp. 467–471 (1984).

Haynes, Johnson, Jr. et al., Erythro–9–(2–hydroxy–3–nonyl) adenine inhibits cyclic–3',5'–guanosine monophosphate–stimulated phosphodiesterase to reverse hypoxic pulmonary vasoconstriction in the perfused rat lung, J. Pharmacol. Exp. Ther. (1996), 276(2), 752–7.

Hidaka, H. et al., Selective Inhibitors of Three Forms of Cyclic Nucleotide Phosphodiesterase—Basic and Potential Clinical Applications, vol. 16, Advances in Cyclic Nucleotide and Protein Phosphorylation Research, pp. 245–259 (1984).

Hucker, H.B. et al., Drug Metabolism & Disposition, vol. 1, No. 6, pp. 721–736 (1973).

Janik, P. et al., Inhibition of Growth of Primary and Metastatic Lewis Lung Carcinoma Cells by the Phosphodiesterase Inhibitor Isobutylmethylxanthine, Cancer Res. vol. 40, pp. 1950–1954, (Jun., 1980).

Jiang, X. et al., Inhibition of calmodulin–dependent phosphodiesterase induces apoptosis in human leukemic cells, Proc. Natl. Acad. Sci. USA, vol. 83, pp. 11236–11241, Oct. 1996.

Kakkar R. et al., Calmodulin–dependent cyclic nucleotide phosphodiesterase (PDE1), Cell Mol. Life Sci. 1999 Jul.;55(8–9):1164–86.

Kodama, K. et al., Effects of a novel, selective and potent phosphodiesterase type V inhibitor, E4021, on myocardial ischemic in guinea pigs, Euro. J. of Pharma. 263, pp. 93–99 (1994).

Korinek, V. et al., Constitutive Transcriptional Activation by a β–Catenin–Tcf Complex in APC$^{-/-}$Colon Carcinoma, Science, vol. 275, pp. 1784–1786, Mar. 21, 1997.

Kozai, Shigetada et al., Synthesis and biological activity of 9–(2,6–difluorobenzyl)–9H–purines bearing chlorine, Chem. Pharm. Bull. (1999), 47(4), 574–575.

Laasberg T. et al., Nerve growth factor increases the cyclic GMP level and activates the cyclic GMP phosphodiesterase in PC12 cells, FEBS Lett. 1988 Nov. 7;239(2):367–70.

Law P.Y. et al., delta–Opioid receptor activates cAMP phosphodiesterase activities in neuroblastoma x glioma NG108–15 hybrid cells, Mol. Pharmacol. 1993 May;43(5):684–93.

Leach M.O. et al., Measurements of human breast cancer using magnetic resonance spectroscopy: a review of clinical measurements and a report of localized 31P measurements of response to treatment, NMR Biomed. 1998 Nov.;11(7):314–40.

Lichtner R. et al., Antimetastatic action of RX–RA 69, a new potent PDE–inhibitor in the Lewis lung carcinoma of the mouse, Prog. Clin. Biol. Res. 1982;89:131–41.

Lichtner, R. B. et al., The Pyrimido–pyrimidine Derivatives RA 233 and RX–RA 85 affect Growth and Cytoskeletal Organization of Rat Mammary Adenocarcinoma Cells, Eur. J. Cancer Clin. Oncol., vol. 23, No. 9, pp. 1269–1275 (1987).

Lichtner, Rosemarie B. et al., The pyrimidopyrimidine derivatives RA233 and RX–RA85 affect cell cycle distribution of two murine tumor cell lines, Eur. J. Cancer Clin. Oncol. 25(6) pp. 945–951 (1989).

Liu, Leo X. et al., Formation of cyclooxygenase–derived eicosanoids by a parasitic intravascular nematode, Adv. Prostaglandin, Thromboxane, Leukotriene Res. (1990), 21B (Prostaglandins Relat. Compd.), 509–12.

Luginer, C. et al., Selective Inhibition of Cyclic Nucleotide Phosphodiesterases of Human, Bovine and Rat Aorta, Biochem. Pharmacology, vol. 35, No. 10, pp. 1743–1751 (1986).

Mahmoud, N. et al., Apc Gene Mutation is Associated with a Dominant–Negative Effect upon Intestinal Cell Migration, Cancer Research 57, pp. 5045–5050, Nov. 15, 1997.

Mahmoud, N. et al., Genotype–Phenotype Correlation in Murine Apc Mutation: Differences in Enterocyte Migration and Response to Sulindac, Cancer Research 59, pp. 353–359, Jan. 15, 1999.

Makaryan, A.P. et al., Cyclic Nucleotides in Patients with Malignant Neoplasms of the Colon, Laboratornoe Delo, vol. 8, pp. 31–33 (1991).

Mamytbekova, A. et al., Antimetastatic effect of flurbiprofen and other platelet aggregation inhibitors (Abstract Only), Neoplasma 33(4), pp. 417–421 (1986).

Marcoz, P. et al., Modulation of rat thymocyte proliferative response through the inhibition of different cyclic nucleotide phosphodiesterase isoforms by means of selective inhibitors and cGMP–elevating agents (Abstract Only), Mol. Pharmacol. 44(5) pp. 1027–1035 (1993).

Marko D. et al., Induction of apoptosis by an inhibitor of cAMP–specific PDE in malignant murine carcinoma cells overexpressing PDE activity in comparison to their nonmalignant counterparts, Cell Biochem Biophys. 1998;28(2–3):75–101.

Mehta, Rajendra et al., Structure–Activity Relationships of Brassinin in Preventing the Development of Carcinogen–Induced Mammary Lesions in Organ Culture, Anticancer Research 14: 1209–1214 (1994).

Mery, Pierre–Francois et al., EHNA as an inhibitor of PDE2: A pharmacological and biochemical study in cardiac myocytes, Phosphodiesterase Inhib. (1996), 81–88.

Michie, Alison M. et al., Rapid regulation of PDE–2 and PDE–4 cyclic AMP phosphodiesterase activity following ligation of the T cell antigen receptor on thymocytes: analysis using the selective inhibitors erythro–9–(2–hydroxy–3–nonyl)–adenine (EHNA) and rolipram, Cell. Signalling (1996), 8(2), 97–110.

Mitchell, J.A. et al., Selectivity of nonsteroidal antiinflammatory drugs as inhibitors of constitutive and inducible cyclooxygenase; Proc. Natl. Acad. Sci. USA, vol. 90, Dec. 1994, pp. 11693–11697.

Molnar–Kimber, K. et al., Modulation of TNFa and IL–1B from indotoxin–stimulated monocytes by selective PDE isozyme inhibitors (Abstract Only), Agents Actions 39(Spec. Conf. Issue), C77–C79 (1993).

Molnar–Kimber, K. L. et al., Differential regulation of TNF–a and IL–1B production from endotoxin stimulated human monocytes by phosphodiesterase inhibitors (Abstract Only), Mediators Inflammation 1(6) pp. 411–417 (1992).

Moorghen, M. et al., Acta Histochemica, Suppl.–Band XXIX, S. 195–199 (1990).

Moorghen, M. et al., Journal of Pathology, vol. 156, pp. 341–347 (1988).

Morgan A.J. et al., Comparison of the effect of isobutylmethylxanthine and phosphodiesterase–selective inhibitors on cAMP levels in SH–SY5Y neuroblastoma cells, Biochem. Pharmacol. 1993 Jun. 22;45(12):2373–80.

Morin, P. et al., Activation of β–Catenin–Tcf Signaling in Colon Cancer by Mutations in β–Catenin or APC, Science, vol. 275, pp. 1787–1789, Mar. 21, 1997.

Murray, K.J. et al., Potential Use of Selective Phosphodiesterase Inhibitors in the Treatment of Asthma, New Drugs for Asthma Therapy, Birkhauser Verlag Basel, pp. 27–46 (1991).

Nagai T. et al., Distinct isozyme patterns of cyclic nucleotide phosphodiesterase in human neuroblastoma and ganglioneuroma; a possible market of differentiation of neural crest––derived tumors and Schwann cells, Jpn. J. Cancer Res. 1986 Jan.; 77(1):52–8.

Nakai A. et al., High Activity of cyclic 3',5'–nucleotide phosphodiesterase in sera of patient with phaeochromocytoma, Clin. Endocrinol. (Oxf) 1986 Apr.;24(4):409–14.

Naskalski J.W. et al., Correlation of granulocyte intracellular activities of cyclic nucleotide phosphodiesterases with leukocyte count in patients with chronic myelogenous leukaemia, Haematologia (Budap) 1986;19(4):285–92.

Nichols M.R. et al., Tyrosine kinase–independent inhibition of cyclic–AMP phosphodiesterase by genistein and tyrphostin 51, Arch. Biochem. Biophys. 1999 Jun. 15;366(2):224–30.

Nicholson, C.D. et al. Differential modulation of tissue function and therapeutic potential of selective inhibitors of cyclic nucleotide phosphodiesterase isoenzymes, Trends Pharmacol. Sci. (TiPS), vol. 12, pp. 19–27 (1991).

O'Donnell, James M. et al., Behavioral effects of family––selective inhibitors of cyclic nucleotide phosphodiesterases, Pharmacol., Biochem. Behav. (1999), 63(1), 185–192.

Oldham S.B. et al., Presence of calmodulin in parathyroid adenomas, Miner Electrolyte Metab. 1982;7(5):273–80.

Patel, V. et al., Plasma cAMP and cAMP–phosphodiesterase (PDE) levels in cancer patients before and after surgery, Indian J. Cancer 1981 Sep.;18(3):181–4.

Peifer, M., β–Catenin as Oncogene: The Smoking Gun, Science, vol. 275, pp. 1752–1753, Mar. 21, 1997.

Pepin, P. et al., Effects of Sulindac and Oltipraz on the tumorigenicity of 4–(methylnitrosamino)1–(3–pyridyl)–1–Butanone in A/J mouse lung, Carcinogenesis vol. 13 No. 3 pp. 341–348 (1992).

Porter, Roderick et al., Preparation of 6–phenyl–3–(5–tetrazoly)pyridin–2(H)–one derivatives as cyclic AMP–dependent protein kinase agonists (Abstract Only), PCT Int. Appl. WO9206085 A1, (Sep. 26, 1991).

Radomski, Marek W. et al., Human Colorectal adenocarcinoma cells: differential nitric oxide synthesis determines their ability of aggregate platelets (Abstract Only), Cancer Res. 51(22) pp. 6073–6078 (1991).

Raeburn, David et al., Effects of isoenzyme–selective inhibitors of cyclic nucleotide phosphodiesterase on microvascular leak in guinea pig airways in vivo (Abstract Only), J. Pharmacol. Exp. Ther., 267(3), pp. 1147–1151 (1993).

Redmond O.M., Tissue characterization and assessment of preoperative chemotherapeutic response in musculoskeletal tumors by in vivo 31P magnetic resonance spectroscopy, Magn. Reson. Med. 1992 Oct.;27(2):226–37.

Rivet–Bastide, Michele et al., cGMP–stimulated cyclic nucleotide phosphodiesterase regulates the Basal calcium current in human atrial myocytes, J. Clin. Invest. (1997), 99(11), 2710–2718.

Rosman, Guy J. et al., Isolation and characterization of human cDNAs encoding a cGMP–stimulated 3',5'–cyclic nucleotide phosphodiesterase, Gene (1997), 191(1), 89–95.

Rubinfeld, B. et al., Stabilization of β–Catenin by Genetic Defects in Melanoma Cell Lines, Science, vol. 275, pp. 1790–1792, Mar. 21, 1997.

Sadhu, Krishna et al., Differential expression of the cyclic GMP–stimulated phosphodiesterase PDE2A in human venous and capillary endothelial cells, J. Histochem. Cytochem. (1999), 47(7), 895–905.

Saeki, T. et al., Isolation of Cyclic Nucleotide Phosphodiesterase Isozymes From Pig Aorta, Biochem. Pharmacology, vol. 46, No. 5, pp. 833–839 (1993).

Savini F. et al., Phosphodiesterase in human colon carcinoma cell line CaCo–2 in culture, Life Sci. 1995;56(22):PL421–5.

Schudt, Christian et al., "Phosphodiesterase Inhibitors"The Handbook of Immunopharmacology, Academic Press, 1996, pp. 65–134.

Semmler, J. et al., Xanthine derivatives: comparison between suppression of tumor necrosis factor–x production and inhibition of cAMP phosphodiesterase activity, Immunology 78, pp. 520–525 (1993).

Shen, T.Y. et al., Chemical and Biological Studies on Indomethacin, Sulindac and Their Analogs, pp. 170–178 (circa 1975).

Sheth S.B. et al., Isolation and regulation of the cGMP–inhibited cAMP phosphodiesterase in human erythroleukemia cells, Thromb. Haemost 1997 Jan.;77(1):155–62.

Silvola, J. et al., Effects of nonsteroidal anti–inflammatory drugs on rat gastric mucosal phosphodiesterase activity, Agents and Actions, vol. 12.4, pp. 516–520 (1982).

Singh R.P. et al., Plasma c–AMP and c–AMP–PDE activity in carcinoma of uterine cervix, Mater Med. Pol. 1988 Apr.–Jun.;20(2):76–8.

Solntseva T.I. et al., [Some feature of cyclic adenosine monophosphate metabolism in mouse liver and hepatoma 22] (Article in Russian), Biokhimiia 1977 Jul.; 42(7):1331–7.

Souness, John E. et al., Role of Selective cyclic GMP phosphodiesterase inhibition in the myorelaxant actions of M&B 22,943, MY–5445, vinpocetine and 1–methyl–3–isobutyl–8–(methylamino)xanthine (Abstract Only), Br. J. Pharmacol. 98(3) pp. 725–734 (1989).

Stevens R.H. et al., Adenosine 3',5'–cyclic monophosphate and guanosine 3',5'–cyclic monophosphate phosphodiesterase activities in 1,2–demethylhydrazine induced colon adenocarcinoma, Cancer Lett. 1979 Aug.;7(4):227–34.

Stevens R.H. et al., Adenosine and guanosine 3',5'–cyclic monophosphate phosphodiesterase activities in rat small and large bowel following single and multiple exposure to 1,2–demethylhydrazine, Drug Chem. Toxicol. 1981;4(2):161–72.

Torphy T.J. et al., Stimulation of beta adrenoceptors in a human monocyte cell line (U937) up–regulates cyclic AMP–specific phosphodiesterase activity, J. Pharmacol. Exp. Ther. 1992 Dec.;263(3):1195–205.

Tsou, K–C. et al. 5'–Nucleotide Phosphodiesterase Isozyme–V as a Marker for Liver Metastases in Breast Cancer Patients, Cancer 54:1788–1793, 1984.

Tulshian, D. et al., Synthesis and Phosphodiesterase Activity of Carboxylic Acid Mimetics of Cyclic Guanosine 3",5"–Monophosphate, J. Med. Chem, vol. 36, 1210–1220 (1993).

Turnbull J.L. et al., The isolation and characterization of cyclic nucleotide phosphodiesterases from Morris hepatoma 5123tc(h) and rat liver, Int. J. Biochem. 184;16(1):19–29 No Date Given.

Turner, N.C. et al., Pulmonary effects of type V cyclic GMP specific phosphodiesterase inhibition in anaesthetized guine-–pig, Br. J. Pharmacol., vol. 111, 1198–1204 (1994).

Turner, N.C. et al., Relaxation of guinea–pig trachea by cyclic AMP phosphodiesterase inhibitors and their enhancement by sodium mitroprusside, Br. J. Pharmacol., vol. III, pp. 1047–1052 (1994).

Tzanakakis G.N. et al., Prevention of human pancreatic cancer cell–induced heaptic metastasis in nude mice by dipyridamole and its analog RA–233, Cancer 1993 Apr. 15;71(8):2466–71.

Van Lookeren Campagne, Michiel M. et al., Characterization of the yeast low Km cAMP–phosphodiesterase with cAMP analogs. Applications in mammalian cells that express the yeast PDE2 gene, J. Biol. Chem. (1990), 265(10), 5847–54.

Verde, Ignacio et al., Characterization of the cyclic nucleotide phosphodiesterase subtypes involved in the regulation of the L–type Ca2+ current in rat ventricular myocytes, Br. J. Pharmacol. (1999), 127(1), 65–74.

Waddell, W.R. et al., Am. J. Surgery, vol. 157, pp. 175–179 (1989).

Waddell, W.R. et al., J. Surg. Oncology, vol. 24, pp. 83–87 (1983).

Weishaar, R.E. et al., A new generation of phosphodiesterase inhibitors: multiple molecular forms of phosphodiesterase and the potential for drug selectivity, J. Med. Chem. 185 May;28(5):537–45 No Date Given.

Weishaar, R.E. et al., Multiple Molecular Forms of Cyclic Nucleotide Phosphodiesterase in Cardiac and Smooth Muscle and In Platelets, Biochem. Pharmacology, vol. 35, No. 5, pp. 787–800 (1986).

Xin Y., [Relationship between cyclic nucleotide phosphodiesterases (cPDE) and some patho–biologic behaviors of stomach cancer—I. Histochemical studies of CPDE in stomach cancer tissues], (Article in Chinese), Chung Hua Chung Liu Tsa Chih 1989 Mar; 11(2):117–20.

Yamashita, Nobuyuki et al., Rolipram, a phosphodiesterase–4–selective inhibitor, promotes the survival of cultured rat dopaminergic neurons, Jpn. J. Pharmacol. (1997), 75(2), 155–159.

Yamashita, Nobuyuki et al., Rolipram, a selective inhibitor of phosphodiesterase type 4, pronouncedly enhanced the forskolin–induced promotion of dopamine biosynthesis in primary cultured rat mesencephalic neurons, Jpn. J. Pharmacol. (1997), 75(1), 91–95.

Yasumoto, T. et al., Properties of Base–Substituted and Carboxyl–Esterified Analogues of Griseolic Acid, a Potent cAMP Phosphodiesterase Inhibitor, Biochemical Pharmacology, vol. 43, No. 10, pp. 2073–2081 (1992).

Zacharski, L. R. et al., Effect of Mopidamol on Survival in Carcinoma of the Lung and Colon: Final Report of Veterans Administration Cooperative Study No. 188, J. of the Nat'l. Cancer Inst., vol. 80, No. 2, pp. 90–96 (1988).

Zacher, L. A; Carey, G.B., Cyclic AMP metabolism by swine adipocyte microsomal and plasma membranes, Comp. Biochem. Physiol., Part B: Biochem. Mol. Biol. (1999), 124B(1), 61–71.

Zurbonsen K. et al., Dissociation between phosphodiesterase inhibition and antiproliferative effects of phosphodiesterase inhibitors on the Dami cell line, Biochem. Pharmacol. 1997 Apr. 25;53(8):1141–7.

Sulindac sulfide

Exisulind

METHODS FOR USING A PHOSPHODIESTERASE IN PHARMACEUTICAL SCREENING TO IDENTIFY COMPOUNDS FOR TREATMENT OF NEOPLASIA

This application is a continuation of serial number 08/866,027 filed May 30, 1997 which is now U.S. Pat. No. 5,858,694.

BACKGROUND OF THE INVENTION

This invention provides a method for identifying compounds potentially useful for the treatment and prevention of pre-cancerous and cancerous lesions in mammals. This application is a continuation of U.S. patent application Ser. No. 08/866,027 to Piazza et al. Filed May 30, 1997.

Familial adenomatous polyposis ("FAP") is an inherited disease where the victim's colon contains many polyps or adenomas virtually uncountable in most instances. Because such patients develop so many polyps or adenomas each of which has a significant risk of developing into a cancer—the typical treatment is surgical removal of the colon. In about 1983, Waddell discovered that the nonsteroidal anti-inflammatory drug ("NSAID") sulindac would cause colonic polyps (a type of pre-cancerous lesion) to regress and prevent their recurrence when that drug was administered to patients with FAP. Waddell's experience with sulindac in FAP patients was confirmed in several subsequent studies. Unfortunately, since sulindac and other NSAIDS aggravate the digestive tract (not to mention side effects involving kidney and interference with normal blood clotting) of patients to whom it has been chronically administered, it is not a practical treatment for FAP or any other cancer or precancerous indication (i.e., neoplasia) requiring long-term administration.

Waddell originally hypothesized that the mechanism of action of sulindac on colonic polyps involved the inhibition of the synthesis of prostaglandin (PG). (Waddell, W. R. et al., "Sulindac for Polyposis of the Colon," *Journal of Surgical Oncology,* 24:83–87, 1983). Prostaglandin ("PG") synthesis inhibition results from the inhibition of cyclooxygenase (COX) caused by NSAIDs. A common benefit of NSAIDs is the reduction of inflammation, which is known to be caused by the reduction of PG levels. Since NSAIDs are known to inhibit COX, which inhibits PG synthesis, it is widely believed that the regression of colonic polyps is attributed to this property. In fact, notwithstanding recent discoveries to the contrary, it has become conventional wisdom that administration of an inhibitor of PG synthesis (e.g., an NSAID) to a patient with FAP or other precancerous or cancerous lesion will result in the regression of the lesion due to a reduction of PG levels.

Recent discoveries, however, are leading scientists in a completely different direction—that it is not necessary to inhibit COX to treat neoplasia patients successfully. Pamukcu et al., in U.S. Pat. No. 5,401,774, disclosed that sulfonyl compounds, that were previously reported to be inactive as PG synthesis inhibitors (and therefore not an NSAID or an anti-inflammatory compound) unexpectedly inhibited the growth of a variety of neoplastic cells, including colon polyp cells. These sulfonyl derivatives have proven effective in rat models of colon carcinogenesis, and one variant (now referred to as exisulind) has proven effective in preliminary human clinical trials with FAP patients.

The importance of this discovery—and the de-linking of anti-neoplasitic activity and COX inhibition—cannot be overstated. If those two phenomena were related, there would be little hope for a safe NSAID therapy for FAP patients because the side effects of NSAIDs, such as gastric irritation, are also caused by COX inhibition. Prostaglandins play a protective function in the lining of the stomach. When NSAIDs are administered, COX is inhibited and PG levels are reduced: gastric irritation is a common result. Those side effects may not manifest themselves in short-term (acute) NSAID therapy. However, during long-term (chronic) NSAID therapy, gastric irritation, bleeding and ulceration are very common. In significant numbers of cases, NSAID therapy must be stopped due to the severity of those side effects and other potentially lethal side effects. Furthermore, the severity of such side effects increases with age, probably because natural PG levels in gastric mucosa falls with age. Thus, useful compounds for treating neoplastic lesions should desirably inhibit neoplastic cell growth, but should not inhibit COX.

Conventional methods for screening compounds may be used to find improved compounds that inhibit neoplastic cell growth. Under this scenario, drugs may be screened using in vitro models. But conventional in vitro screening methods could pass many compounds that later are shown to be ineffective in animal models because of a number of unanticipated problems, one of which may be that the in vitro screen is not predictive of efficacy. Animal model studies are time consuming and expensive. Therefore, a more precise in vitro screening method that provides predictive information for treating neoplasia is needed to screen compounds prior to human testing. Knowledge of a specific target for inhibiting human cancer would allow for greater precision and efficiency whereby highly effective and safe compounds can be identified prior to animal testing.

Presently, rational drug discovery methods are being applied in the pharmaceutical industry to improve methods for identifying clinically useful compounds. Typically, rational drug discovery methods relate to a "lock and key" concept whereby structural relationships between a therapeutic target molecule (lock) and pharmaceutical compounds (key) are defined. Such methods are greatly enhanced by specialty computer software that accesses databases of compounds to identify likely geometric fits with the target molecule. Unfortunately, to use these systems, one has to have insight to the target molecule (lock). The target may be an enzyme, a protein, a membrane or nuclear receptor, or a nucleic acid sequence, for example.

In complex diseases, such as neoplasia, scientists have identified a number of potential targets. However, many of the drugs available for the treatment of neoplasia are non-specific and toxic to normal tissues, and are not indicated for precancer and used only when neoplastic cells progress to cancer. Greater understanding of the mechanisms involved in cancer may lead scientists on the path towards designing more specific antineoplastic drugs—drugs that can safely be administered earlier in the disease process.

SUMMARY OF THE INVENTION

This invention relates to a novel in vitro method for screening test compounds for their ability to treat and prevent neoplasia, especially pre-cancerous lesions, safely. In particular, the present invention provides a method for identifying test compounds that can be used to treat and prevent neoplasia, including precancerous lesions, with minimal side effects associated with COX inhibition and other non-specific interactions.

In one embodiment of this invention, therefore, the screening method involves determining the COX inhibition activity of a test compound. Because the inventors have discovered a relationship between inhibition of cancer and inhibition of phosphodiesterase Type-5 isoenzyme ("PDE5"), this invention includes determining the PDE5 inhibition activity of the compound. Preferably, the screening method of this invention further includes determining whether the compounds inhibit the growth of tumor cells in a cell culture.

In an alternate embodiment, the screening method of this invention involves determining the COX inhibition activity of the compound, determining the PDE5 inhibition activity of the compound and determining whether the compound induces apoptosis in tumor cells.

By screening compounds in this fashion, potentially beneficial and improved compounds can be identified more rapidly and with greater precision than possible in the past. Further benefits will be apparent from the detailed description that follows.

DETAILED DESCRIPTION OF THE PREFERRED EMBODIMENTS

Figure 1:
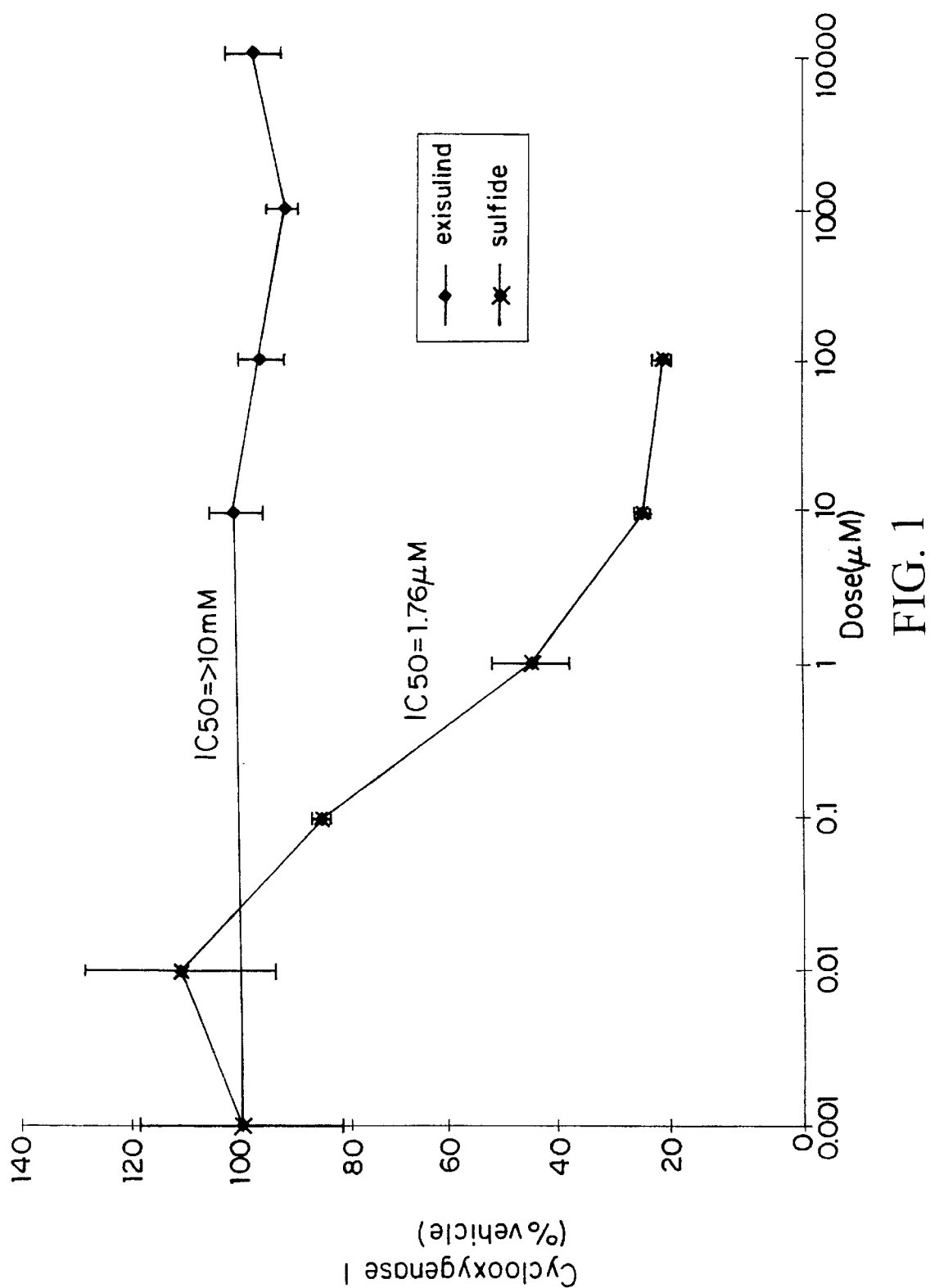
FIG. 1 illustrates the effect of the sulfide derivative of sulindac and the sulfone derivative of sulindac (a.k.a. exisulind) on purified cyclooxygenase activity.

The method of this invention is useful to identify compounds that can be used to treat or prevent neoplasms, and which are not characterized by the serious side effects of conventional NSAIDs.

Cancer and precancer may be thought of as diseases that involve unregulated cell growth. Cell growth involves a number of different factors. One factor is how rapidly cells proliferate, and another involves how rapidly cells die. Cells can die either by necrosis or apoptosis depending on the type of environmental stimuli. Cell differentiation is yet another factor that influences tumor growth kinetics. Resolving which of the many aspects of cell growth is affected by a test compound is important to the discovery of a relevant target for pharmaceutical therapy. Screening assays based on this selectivity can be combined with tests to determine which compounds having growth inhibiting activity.

This invention is the product of several important discoveries. First, the present inventors discovered that desirable inhibitors of tumor cell growth induce premature death of cancer cells by apoptosis (see, Piazza, G. A., et al., *Cancer Research*, 55(14), 3110–16, 1995). Second, the present inventors unexpectedly discovered that compounds that selectively induce apoptosis without substantial COX inhibition also inhibit phosphodiesterase ("PDE"). In particular, and contrary to leading scientific studies, desirable compounds for treating neoplastic lesions selectively inhibit Type 5 isoenzyme form of phosphodiesterase ("PDE5") (EC 3.1.4.17). PDE5 is one of at least seven isoenzymes of phosphodiesterase. PDE5 is unique in that it selectively degrades cyclic GMP, while the other types of PDE are either non-selective or degrade cyclic AMP. Preferably, desirable compounds do not substantially inhibit other phosphodiesterase types.

A preferred embodiment of the present invention involves determining the cyclooxygenase inhibition activity of a given compound, and determining the PDE5 inhibition activity of the compound. The test compounds are scored for their probable ability to treat neoplastic lesions either directly by assessing their activities against specific cutoff values or indirectly by comparing their activities against known compounds useful for treating neoplastic lesions. A standard compound that is known to be effective for treating neoplastic lesions without causing gastric irritation is 5-fluoro-2-methyl-1-(p-methylsulfonylbenzylidene)-3-indenylacetic acid ("exisulind"). Other useful compounds for comparative purposes include those that are known to inhibit COX, such as indomethacin and the sulfide metabolite of sulindac: 5-fluoro-2-methyl-1-(p-methylsulfinylbenzylidene)-3-indenylacetic acid ("sulindac sulfide"). Other useful compounds for comparative purposes include those that are known to inhibit PDE5, such as 1-(3-chloroanilino)-4-phenyphthalazine ("MY5445").

A test compound is clearly determined to be a promising candidate if it performs better than or comparable to exisulind and does not inhibit COX. In general, desirable compounds are those that inhibit PDE5 and inhibit cell growth and induce apoptosis, but do not inhibit COX at pharmacologically accepted doses.

As used herein, the term "precancerous lesion" includes syndromes represented by abnormal neoplastic, including dysplastic, changes of tissue. Examples include dysplastic growths in colonic, breast, prostate or lung tissues, or conditions such as dysplastic nevus syndrome, a precursor to malignant melanoma of the skin. Examples also include, in addition to dysplastic nevus syndromes, polyposis syndromes, colonic polyps, precancerous lesions of the cervix (i.e., cervical dysplasia), esophagus, lung, prostatic dysplasia, prostatic intraneoplasia, breast and/or skin and related conditions (e.g., actinic keraosis), whether the lesions are clinically identifiable or not.

As used herein, the term "carcinoma" or "cancer" refers to lesions which are cancerous. Examples include malignant melanomas, breast cancer, prostate cancer and colon cancer. As used herein, the terms "neoplasia" and "neoplasms" refer to both cancerous and pre-cancerous lesions.

As used herein, the abbreviation PG represents prostaglandin; PS represents prostaglandin synthetase; $PGE_2$ represents prostaglandin $E_2$; PDE represents phosphodiesterase; COX represents cyclooxygenase; RIA represents—radioimmunoassay.

As used herein, "PDE5" refers to that enzyme and any of its isoforms that exhibit cGMP specific hydrolytic enzyme activities and high affinity cGMP binding.

In another aspect of the invention, there is a method for treating patients in need of treatment for neoplasia by identifying compounds that exhibit substantial PDE5 inhibitory activity at pharmacologically acceptable doses, and administering one or more of those compounds to a patient in need thereof with neoplasia sensitive to the compound.

SCREENING PROTOCOLS

The following screening protocols, and alternative protocols, are provided to aid in the understanding of the preferred methods used to screen test compounds to determine their potential to treat or prevent neoplasia, especially pre-cancerous lesions.

1. Determining COX Inhibitory Activity

COX inhibition can be determined by either of two methods. One method involves measuring $PGE_2$ secretion by intact HL-60 cells following exposure to the compound being screened. The other method involves measuring the activity of purified cyclooxygenases (COXs) in the presence of the compound. Both methods involve protocols previously described in the literature.

1.A. $PGE_2$ secretion

Compounds of this can be evaluated to determine whether they inhibited the production of prostaglandin $E_2$ ("$PGE_2$"), according to procedures known in the art. For example, $PGE_2$ secreted from a cell can be measured using an enzyme immunoassay (EIA) kit for $PGE_2$, such as commercially available from Amersham, Arlington Heights, Ill USA. Suitable cells include those which make an abundance of PG, such as HL-60 cells. HL-60 cells are human promyelocytes that are differentiated with DMSO in mature granulocytes. (See, Collins, S. J., Ruscetti, F. W., Gallagher, R. E. and Gallo, R. C., "Normal Functional Characteristics of Cultured Human Promyelocytic Leukemia Cells (HL-60) After Induction of Differentiation By Dimethylsulfoxide", *J. Exp. Med.*, 149:969–974, 1979). These differentiated cells produce $PGE_2$ after stimulation with a calcium ionophore A23187 (see, Kargman, S., Prasit, P. and Evans, J. F., "Translocation of HL-60 Cell 5-Lipoxygenase", *J. Biol. Chem.*, 266: 23745–23752, 1991). HL-60 are available from the American Type Culture Collection (ATCC:CCL240). They can be grown in a RPMI 1640 medium supplemented with 20% heat-inactivated fetal bovine serum, 50 U/ml penicillin and 50 μg/ml streptomycin in an atmosphere of 5% $CO_2$ at 37° C. To induce myeloid differentiation, cells are exposed to 1.3% DMSO for 9 days and then washed and resuspended in Dulbecco's phosphate-buffered saline at $3\times10^6$ cells/ml.

The differentiated HL-60 cells ($3\times10^6$ cells/ml) can be incubated for 15 min at 37° C. in the presence of the compounds tested at the desired concentration. Cells are then stimulated by A23187 ($5\times10^{-6}$ M) for 15 min. $PGE_2$ secreted into the external medium is measured as described above.

1.B Purified cyclooxygenases

Two different forms of cyclooxygenase (COX-I and COX-2) have been reported in the literature to regulate prostaglandin synthesis. It is known that COX-2 represents the inducible form of COX while COX-I represents a constitutive form. COX-I activity can be measured using the method described by Mitchell et al. ("Selectivity of Non-steroidal Anti-inflammatory Drugs as Inhibitors of Constitutive and Inducible Cyclooxygenase," *Proc. Natl. Acad. Sci. USA.*, 90:11693–11697, 1993, which is incorporated herein by reference) using COX-I purified from ram seminal vesicles as described by Boopathy & Balasubramanian, "Purification And Characterization Of Sheep Platelet Cyclooxygenase" (*Biochem. J.*, 239:371–377, 1988, which is incorporated herein by reference). COX-2 activity can be measured using COX-2 purified from sheep placenta as described by Mitchell et al., 1993, supra.

The cyclooxygenase inhibitory activity of a drug can be determined by methods known in the art. For example, Boopathy & Balasubramanian, 1988, supra, described a procedure in which prostaglandin H synthase 1 (Cayman Chemical, Ann Arbor, Mich.) is incubated at 37° C. for 20 min with 100 μM arachidonic acid (Sigma Chemical Co.), cofactors (such as 1.0 mM glutathione, 1.0 mM hydroquinone, 0.625 μM hemoglobin and 1.25 mM $CaCl_2$ in 100 mM Tris-HCl, pH 7.4) and the drug to be tested. Following incubation, the reaction can be terminated with trichloroacetic acid. Enzymatic activity can then be measured spectrophotometrically at 530 nm after stopping the reaction by adding thiobarbituric acid and malonaldehyde.

Obviously, a compound that exhibits minimal COX-I or COX-2 inhibitory activity in relation to its greater PDE5 inhibitory activity may not be entirely undesirable.

1.C. Analyzing Results

The amount of inhibition is determined by comparing the activity of the cyclooxygenase in the presence and absence of the test compound. Residual or no COX inhibitory activity (i.e., less than about 25%) at a concentration of about 100 μM is indicative that the compound should be evaluated further for usefulness for treating neoplasia. Preferably, the $IC_{50}$ concentration should be greater than 1000 μM for the compound to be further considered potential use.

2. Determining Phosphodiesterase (PDE5) Inhibition Activity

Compounds can be screened for inhibitory effect on phosphodiesterase activity using either the enzyme isolated from any tumor cell line such as HT-29 or SW-480, or recombinant HS-PDE5, for example, or measuring cyclic nucleotide levels in whole cells.

2.A. Enzyme Assay

Phosphodiesterase activity can be determined using methods known in the art, such as a method using radioactive $^3$H cyclic GMP (cGMP)(cyclic 3',5'-guanosine monophosphate) as the substrate for PDE5 enzyme. (Thompson, W. J., Teraski, W. L., Epstein, P. M., Strada, S. J., *Advances in Cyclic Nucleotide Research*, 10:69–92, 1979, which is incorporated herein by reference). In brief, a solution of defined substrate $^3$H-cGMP specific activity (0.2 μM; 100,000 cpm; containing 40 mM Tris-HCl (pH 8.0), 5 MM $MgCl_2$ and 1 mg/ml BSA) is mixed with the drug to be tested in a total volume of 400 μl. The mixture is incubated at 30° C. for 10 minutes with partially purified PDE5 isolated from HT-29 cells. Reactions are terminated, for example, by boiling the reaction mixture for 75 seconds. After cooling on ice, 100 μl of 0.5 mg/ml snake venom (*O. Hannah* venom available from Sigma) is added and incubated for 10 min at 30° C.

This reaction is then terminated by the addition of an alcohol, e.g. 1 ml of 100% methanol. Assay samples are applied to a anion chromatography column (1 ml Dowex, from Aldrich) and washed with 1 ml of 100% methanol. The amount of radioactivity in the breakthrough and the wash from the columns in then measured with a scintillation counter. The degree of PDE5 inhibition is determined by calculating the amount of radioactivity in drug-treated reactions and comparing against a control sample (a reaction mixture lacking the tested compound).

2.B. Cyclic Nucleotide Measurements

Alternatively, the ability for desirable compounds to inhibit PDE5 is reflected by an increase in cGMP in neoplastic cells exposed to a compound being screened. The amount of PDE5 activity can be determined by assaying for the amount of cyclic GMP in the extract of treated cells using radioimmunoassay (RIA). In this procedure, HT-29 or SW-480 cells are plated and grown to confluency. The test compound is then incubated with the cell culture at a concentration of compound between about 200 $\mu$M to about 200 pM. About 24 to 48 hours thereafter, the culture media is removed from the cells, and the cells are solubilized. The reaction is stopped by using 0.2 N HCl/50% MeOH. A sample is removed for protein assay. Cyclic GMP is purified from the acid/alcohol extracts of cells using anion-exchange chromatography, such as a Dowex column. The cGMP is dried, acetylated according to published procedures, such as using acetic anhydride in triethylamine, (Steiner, A. L., Parker, C. W., Kipnis, D. M., *J Biol. Chem.*, 247(4):1106–13, 1971, which is incorporated herein by reference). The acetylated cGMP is quantitated using radioimmunoassay procedures (Harper, J., Brooker, G., *Advances in Nucleotide Research*, 10:1–33, 1979, which is incorporated herein by reference). Iodinated ligands (tyrosine metheyl ester) of derivatized cyclic GMP are incubated with standards or unknowns in the presence of antisera and appropriate buffers. Antiserum may be produced using cyclic nucleotide-haptene directed techniques. The antiserum is from sheep injected with succinyl-cGMP-albumin conjugates and diluted 1/20,000. Dose-interpolation and error analysis from standard curves are applied as described previously (Seibert, A. F., Thompson, W. J., Taylor, A., Wilbourn, W. H., Barnard, J. and Haynes, J., *J. Applied Physiol*, 72:389–395, 1992, which is incorporated herein by reference).

In addition, the culture media may be acidified, frozen (–70° C.) and also analyzed for cGMP and cAMP.

In addition to observing increases in content of cGMP caused by desirable test compounds, decreases in content of cAMP have been observed. It has been observed that a particularly desirable compound (i.e. one that selectively induces apoptosis in neoplastic cells, but not substantially in normal cells) follows a time course consistent with PDE5 inhibition as one initial action resulting in an increased cGMP content within minutes. Secondarily, treatment of neoplastic cells with a desirable anti-neoplastic compound leads to decreased cAMP content within 24 hours. The intracellular targets of drug actions are being studied further, but current data supports the concept that both the initial rise in cGMP content followed by the subsequent fall in cAMP content precede apoptosis in neoplastic cells exposed to desirable compounds.

The change in the ratio of the two cyclic nucleotides may be a more accurate tool for evaluating desirable PDE5 inhibition activity of test compounds, rather than measuring only the absolute value of cGMP, only PDE5 inhibition, or only the absolute value of cGMP. In neoplastic cells not treated with anti-neoplastic compounds, the ratio of cGMP content/cAMP content is in the 0.03–0.05 range (i.e., 300–500 fmol/mg protein cGMP content over 6000–8000 fmol/mg protein cAMP content). After exposure to desirable anti-neoplastic compounds, that ratio increases several fold (preferably at least about a three-fold increase) as the result of an initial increase in cyclic GMP and the later decrease in cyclic AMP.

Specifically, it has been observed that particularly desirable compounds achieve an initial increase in cGMP content in treated neoplastic cells to a level of cGMP greater than about 500 fmol/mg protein. In addition, particularly desirable compounds cause the later decrease in cAMP content in treated neoplastic cells to a level of cAMP less than about 4000 fmol/mg protein.

To determine the content of cyclic AMP, radioimmunoassay techniques similar to those described above for cGMP are used. Basically, cyclic nucleotides are purified from acid/alcohol extracts of cells using anion-exchange chromatography, dried, acetylated according to published procedures and quantitated using radioimmunoassay procedures. Iodinated ligands of derivatized cyclic AMP and cyclic GMP are incubated with standards or unknowns in the presence of specific antisera and appropriate buffers.

Verification of the cyclic nucleotide content may be obtained by determining the turnover or accumulation of cyclic nucleotides in intact cells. To measure inteact cell cAMP, $^3$H-adenine prelabeling is used according to published procedures (Whalin M. E., R. L. Garrett Jr., W. J. Thompson, and S. J. Strada, "Correlation of cell-free brain cyclic nucleotide phosphodiesterase activities to cyclic AMP decay in intact brain slices", *Sec. Mess. and Phos. Protein Research*, 12:311–325, 1989, which is incorporated herein by reference). The procedure measures flux of labeled ATP to cyclic AMP and can be used to estimate intact cell adenylate cyclase or cyclic nucleotide phosphodiesterase activities depending upon the specific protocol. Cyclic GMP accumulation was too low to be studied with intact cell prelabeling according to published procedures (Reynolds, P. E., S. J. Strada and W. J. Thompson, "Cyclic GMP accumulation in pulmonary microvascular endothelial cells measured by intact cell prelabeling," *Life Sci.*, 60:909–918, 1997, which is incorporated herein by reference).

2.C. Tissue sample assay

The PDE5 inhibitory activity of a test compound can also be determined from a tissue sample. Tissue samples, such as mammalian (preferably rat) liver, are collected from subjects exposed to the test compound. Briefly, a sample of tissue is homogenized in 500 $\mu$l of 6% TCA. A known amount of the homogenate is removed for protein analysis. The remaining homogenate is allowed to sit on ice for 20 minutes to allow for the protein to precipitate. Next, the homogenate is centrifuged for 30 minutes at 15,000g at 4° C. The supernatant is recovered and the pellet recovered. The supernatant is washed four times with five volumes of water saturated diethyl ether. The upper ether layer is discarded between each wash. The aqueous ether extract is dried in a speed vac. Once dried, the sample can be frozen for future use, or used immediately. The dried extract is dissolved in 500 $\mu$l of assay buffer. The amount of PDE5 inhibition is determined by assaying for the amount of cyclic nucleotides using an enzyme immunoassay (EIA), such as the Biotrak EIA system acetylation protocol (available from Amersham, Arlington Heights, Ill., USA). Alternatively, RIA procedures as detailed above may be used.

2.D. Analyzing Results

The amount of inhibition is determined by comparing the activity of PDE5 in the presence and absence of the test compound. Inhibition of PDE5 activity is indicative that the compound is useful for treating neoplasia. Significant inhibitory activity greater than that of the benchmark, exisulind, preferably greater than 50% at a concentration of 10 μM or below, is indicative that a compound should be further evaluated for antineoplastic properties. Preferably, the $IC_{50}$ value for PDE5 inhibition should be less than 50 μM for the compound to be further considered for potential use.

3. Determining Whether A Compound Reduces The Number Of Tumor Cells

In an alternate embodiment, the screening method of the present invention involves further determining whether the compound reduces the growth of tumor cells. Various cell lines can be used in the sample depending on the tissue to be tested. For example, these cell lines include: SW-480—colonic adenocarcinoma; HT-29—colonic adenocarcinoma; A-427—lung adenocarcinoma carcinoma; MCF-7—breast adenocarcinoma; and UACC-375—melanoma line; and DU145—prostrate carcinoma. Cytotoxicity data obtained using these cell lines are indicative of an inhibitory effect on neoplastic lesions. These cell lines are well characterized, and are used by the United States National Cancer Institute in their screening program for new anti-cancer drugs.

3A. Tumor Inhibition in HT-29 Cell Line

A compound's ability to inhibit tumor cell growth can be measured using the HT-29 human colon carcinoma cell line obtained from ATCC (Bethesda, Md.). HT-29 cells have previously been characterized as relevant colon tumor cell culture model (Fogh, J., and Trempe, G. In: Human Tumor Cells in Vitro, J. Fogh (eds.), Plenum Press, New York, pp. 1 15–159, 1975). HT-29 cells are maintained in RPMI media supplemented with 5% fetal serum (Gemini Bioproducts, Inc., Carlsbad, Calif.) and 2 mm glutamine, and 1% antibiotic-antimycotic in a humidified atmosphere of 95% air and 5% $CO_2$ at 37° C. Briefly, HT-29 cells are plated at a density of 500 cells/well in 96 well microtiter plates and incubated for 24 hours at 37° C. prior to the addition of compound. Each determination of cell number involved six replicates. After six days in culture, the cells are fixed by the addition of cold trichloroacetic acid to a final concentration of 10% and protein levels are measured using the sulforhodamine B (SRB) calorimetric protein stain assay as previously described by Skehan, P., Storeng, R., Scudiero, D., Monks, A., McMahon, J., Vistica, D., Warren, J. T., Bokesch, H., Kenney, S., and Boyd, M. R., "New Colorimetric Assay For Anticancer-Drug Screening," J. Natl. Cancer Inst. 82: 1107–1112, 1990, which is incorporated herein by reference.

In addition to the SRB assay, a number of other methods are available to measure growth inhibition and could be substituted for the SRB assay. These methods include counting viable cells following trypan blue staining, labeling cells capable of DNA synthesis with BrdU or radiolabeled thymidine, neutral red staining of viable cells, or MTT staining of viable cells.

3.B. Analyzing Results

Significant tumor cell growth inhibition greater than about 50% at a dose of 100 μM or below is further indicative that the compound is useful for treating neoplastic lesions. Preferably, an $IC_{50}$ value is determined and used for comparative purposes. This value is equivalent to the concentration of drug needed to inhibit tumor cell growth by 50% relative to the control. Preferably, the $IC_{50}$ value should be less than 100 μM for the compound to be considered further for potential use for treating neoplastic lesions.

4. Determining Whether A Compound Induces Apoptosis

In a second alternate embodiment, the screening method of the present invention further involves determining whether the compound induces apoptosis in cultures of tumor cells.

Two distinct forms of cell death may be described by morphological and biochemical criteria: necrosis and apoptosis. Necrosis is accompanied by increased permeability of the plasma membrane; the cells swell and the plasma membrane ruptures within minutes. Apoptosis is characterized by membrane blebbing, condensation of cytoplasm and the activation of endogenous endonucleases.

Of the two, apoptosis is the most common form of eukaryotic cell death. It occurs naturally during normal tissue turnover and during embryonic development of organs and limbs. Apoptosis also is induced by cytotoxic T-lymphocytes and natural killer cells, by ionizing radiation and certain chemotherapeutic drugs. Inappropriate regulation of apoptosis is thought to play an important role in many pathological conditions including cancer, AIDS, Alzheimer disease, etc. Compounds can be screened for induction of apoptosis using cultures of tumor cells maintained under conditions as described above. Treatment of cells with test compounds involves either pre- or post-confluent cultures and treatment for two to seven days at various concentrations. Apoptotic cells are measured in both the attached and "floating" compartments of the cultures. Both compartments are collected by removing the supernatant, trypsinizing the attached cells, and combining both preparations following a centrifugation wash step (10 minutes, 2000 rpm). The protocol for treating tumor cell cultures with sulindac and related compounds to obtain a significant amount of apoptosis has been described in the literature. (See, Piazza, G. A., et al., Cancer Research, 55:3110–16, 1995, which is incorporated herein by reference). The novel features include collecting both floating and attached cells, identification of the optimal treatment times and dose range for observing apoptosis, and identification of optimal cell culture conditions.

4.A. Morphological observation of apoptosis

Following treatment with a test compound, cultures can be assayed for apoptosis and necrosis by fluorescent microscopy following labeling with acridine orange and ethidium bromide. The method for measuring apoptotic cell number has previously been described by Duke & Cohen, "Morphological And Biochemical Assays Of Apoptosis," Current Protocols In Immunology, Coligan et al., eds., 3.17.1–3.17.16 (1992, which is incorporated herein by reference).

For example, floating and attached cells can be collected by trypsinization and washed three times in PBS. Aliquots of cells can be centrifuged. The pellet can then be resuspended in media and a dye mixture containing acridine orange and ethidium bromide prepared in PBS and mixed gently. The mixture can then be placed on a microscope slide and examined.

4.B. Analysis of apoptosis by DNA fragmentation

Apoptosis can also be quantified by measuring an increase in DNA fragmentation in cells which have been treated with test compounds. Commercial photometric EIA for the quantitative in vitro determination of cytoplasmic histone-associated-DNA-fragments (mono- and oligonucleosomes) are available (Cell Death Detection ELISA$^{okys}$, Cat. No. 1,774,425, Boehringer Mannheim). The Boehringer Mannheim assay is based on a sandwich-enzyme-immunoassay principle using mouse monoclonal antibodies directed against DNA and histones, respectively. This allows the specific determination of mono- and oligonucleosomes in the cytoplasmatic fraction of cell lysates.

According to the vendor, apoptosis is measured in the following fashion. The sample (cell-lysate) is placed into a streptavidin-coated microtiter plate ("MTP"). Subsequently, a mixture of anti-histone-biotin and anti-DNA peroxidase conjugate are added and incubated for two hours. During the incubation period, the anti-histone antibody binds to the histone-component of the nucleosomes and simultaneously fixes the immunocomplex to the streptavidin-coated MTP via its biotinylation. Additionally, the anti-DNA peroxidase antibody reacts with the DNA component of the nucleosomes. After removal of unbound antibodies by a washing step, the amount of nucleosomes is quantified by the peroxidase retained in the immunocomplex. Peroxidase is determined photometrically with ABTS7 (2,2'-Azido-[3-ethylbenzthiazolin-sulfonate])* as substrate.

For example, SW-480 colon adenocarcinoma cells are plated in a 96-well MTP at a density of 10,000 cells per well. Cells are then treated with test compound, and allowed to incubate for 48 hours at 37° C. After the incubation, the MTP is centrifuged and the supernatant is removed. The cell pellet in each well is then resuspended in lysis buffer for 30 minutes. The lysates are then centrifuged and aliquots of the supernatant (i.e. cytoplasmic fraction) are transferred into streptavidin coated MTP. Care is taken not to shake the lysed pellets (i.e. cell nucleii containing high molecular weight, unfragmented DNA) in the MTP. Samples are then analyzed.

Fold stimulation ($FS=OD_{max}/OD_{veh}$), an indicator of apoptotic response, is determined for each compound tested at a given concentration. $EC_{50}$ values may also be determined by evaluating a series of concentrations of the test compound.

4.C. Analyzing Results

Statistically significant increases of apoptosis (i.e., greater than 2 fold stimulation at a concentration of 100 μM) are further indicative that the compound is useful for treating neoplastic lesions. Preferably, the $EC_{50}$ value for apoptotic activity should be less than 100 μM for the compound to be further considered for potential use for treating neoplastic lesions. $EC_{50}$ is herein defined as the concentration that causes 50% induction of apoptosis relative to vehicle treatment.

5. VALIDATION—Mammary Gland Organ Culture Model Tests

Test compounds identified by the above methods can be tested for antineoplastic activity by their ability to inhibit the incidence of preneoplastic lesions in a mammary gland organ culture system. This mouse mammary gland organ culture technique has been successfully used by other investigators to study the effects of known antineoplastic agents such as NSAIDs, retinoids, tamoxifen, selenium, and certain natural products, and is useful for validation of the screening method of the present invention.

For example, female BALB/c mice can be treated with a combination of estradiol and progesterone daily, in order to prime the glands to be responsive to hormones in vitro. The animals are sacrificed and thoracic mammary glands are excised aseptically and incubated for ten days in growth media supplemented with insulin, prolactin, hydrocortisone, and aldosterone. DMBA (7,12-dimethylbenz(a)anthracene) is administered to induce the formation of premalignant lesions. Fully developed glands are then deprived of prolactin, hydrocortisone, and aldosterone, resulting in the regression of the glands but not the premalignant lesions.

The test compound is dissolved in DMSO and added to the culture media for the duration of the culture period. At the end of the culture period, the glands were fixed in 10% formalin, stained with alum carmine, and mounted on glass slides. The incidence of forming mammary lesions is the ratio of the glands with mammary lesions and glands without lesions. The incidence of mammary lesions in test compound treated glands is compared with that of the untreated glands.

The extent of the area occupied by the mammary lesions can be quantitated by projecting an image of the gland onto a digitation pad. The area covered by the gland is traced on the pad and considered as 100% of the area. The space covered by each of the unregressed structures is also outlined on the digitization pad and quantitated by the computer.

EXPERIMENTAL SECTION

A number of test compounds were examined in the various protocols and screened for potential use in treating neoplasia. The results of these tests are reported below. The test compounds are hereinafter designated by a letter code that corresponds to the following:

A—rac-threo-(E)-1-(N,N'-diethylaminoethanethio)-1-(butan-1',4'-olido)- [3',4':1,2]-6-fluoro-2-methyl-3-(p-methylsulfonylbenzylidene)-indan;

B—(Z)-5-Fluoro-2-methyl-1-(3,4,5-trimethoxybenzylidene)-3-acetic acid;

C—(Z)-5-Fluoro-2-methyl-1-(p-chlorobenzylidene)-3-acetic acid;

D—rac-(E)-1-(butan-1',4'-olido)-[3',4':1,2]-6-fluoro-2-methyl-3-(p-methylsulfonylbenzylidene)-1S-indanyl-N-acetylcysteine;

E—(Z)-5-Fluoro-2-methyl-1-(3,4,5-trimethoxybenzylidene)-3-indenylacetamide, N-benzyl;

F—(Z)-5-Fluoro-2-methyl-1-(p-methylsulfonylbenzylidene)-3-indenylacetamide, N,N'-dicyclohexyl;

G—ribo-(E)-1-Triazolo-[2',3':1",3"]-1-(butan-1',4'-olido)-[3',4':1,2]-6-fluoro-2-methyl-3-(p-methylsulfonylbenzylidene)-indan; and H—rac-(E)-1-(butan-1',440 -olido)-[3',4':1,2]-6-fluoro-2-methyl-3-(p-methylsulfonylbenzylidene)-1S-indanyl-glutathione).

Example 1—COX inhibition assay

Reference compounds and test compounds were analyzed for their COX inhibitory activity in accordance with the protocol for the COX assay of section 1.B. supra. FIG. 1 shows the effect of various concentrations of either sulindac sulfide or exisulind on purified cyclooxygenase (Type 1) activity. Cyclooxygenase activity was determined using purified cyclooxygenase from ram seminal vesicles as described previously (Mitchell et al, supra). The IC-50 value for sulindac sulfide was calculated to be approximately 1.76 μM, while that for exisulind was greater than 10,000 μM. These data show that sulindac sulfide, but not exisulind, is a COX-I inhibitor. Similar data was obtained for the COX-2 isoenzyme. (Thompson, et al., *Journal of the National Cancer Institute*, 87: 1259–1260, 1995).

Figure 2:
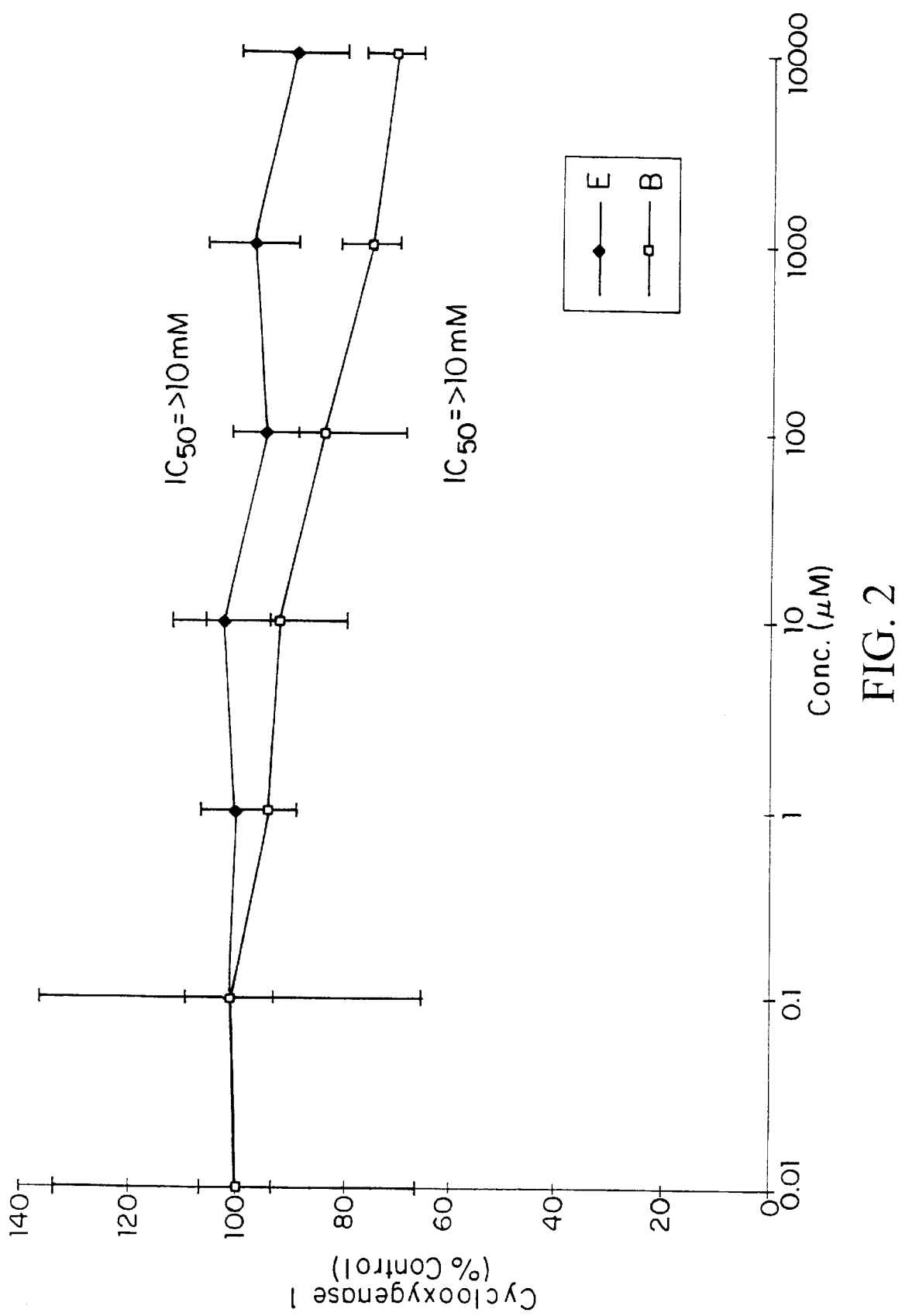
FIG. 2 illustrates the effects of test compounds B and E on COX inhibition.

FIG. 2 shows the effect of test compounds B and E on COX inhibition. COX activity was determined as for the compounds shown in FIG. 1. The data show that both test compound B and E do not significantly inhibit COX-I.

TABLE 1

Cyclooxygenase inhibitory activity among a series of compounds

| Reference compounds | % Inhibition at 100 μM |
|---|---|
| Indomethacin | 95 |
| MY5445 | 94 |

TABLE 1-continued

Cyclooxygenase inhibitory activity among a series of compounds

| | |
|---|---|
| Sulindac sulfide | 97 |
| Exisulind | <25 |

| Test compounds | % Inhibition at 100 µM |
|---|---|
| A | <25 |
| B | <25 |
| C | 87 |
| D | <25 |
| E | <25 |

In accordance with the protocol of section 1.B., supra, compounds A through E were evaluated for COX inhibitory activity as reported in Table 1 above. Compound C was found to inhibit COX greater than 25% at a 100 µM dose, and therefore, would not be selected for further screening.

Example 2—PDE5 inhibition assay

Figure 3:
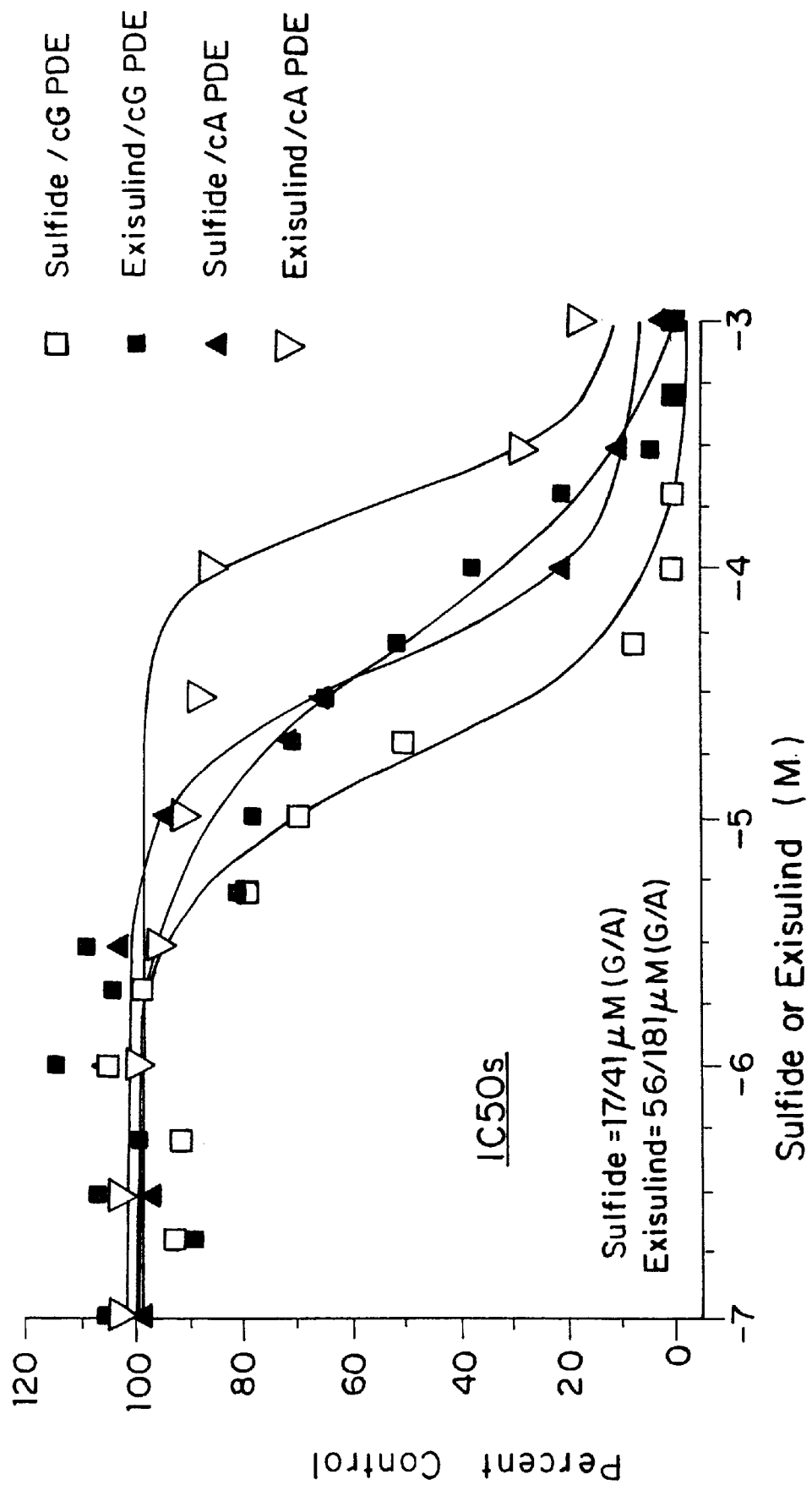
FIG. 3 illustrates the inhibitory effects of sulindac sulfide and exisulind on PDE-4 and PDE5 purified from cultured tumor cells.

Reference compounds and test compounds were analyzed for their PDE5 inhibitory activity in accordance with the protocol for the assay of section 2.A., supra. FIG. 3 shows the effect of various concentrations of sulindac sulfide and exisulind on either PDE-4 or PDE5 activity purified from human colon HT-29 cultured tumor cells, as described previously (W. J. Thompson et al., supra). The $IC_{50}$ value of sulindac sulfide for inhibition of PDE4 was 41 µM, and for inhibition of PDE5 was 17 µM. The $IC_{50}$ value of exisulind for inhibition of PDE4 was 181 µM, and for inhibition of PDE5 was 56 µM. These data show that both sulindac sulfide and exisulind inhibit phosphodiesterase activity. Both compounds show selectivity for the PDE5 isoenzyme form.

Figure 4A:
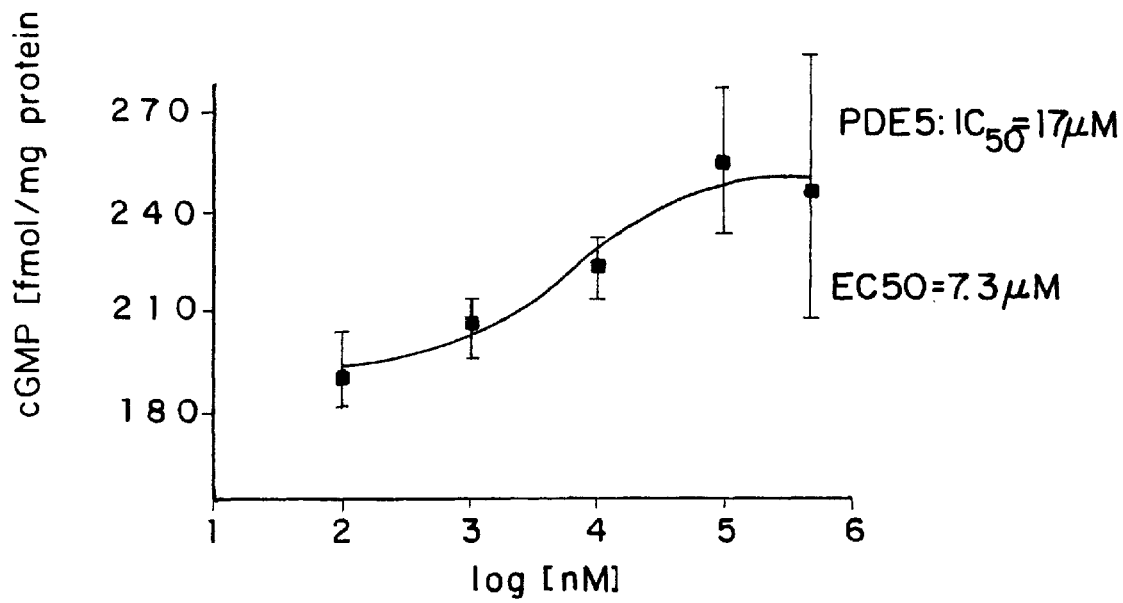
FIG. 4 illustrates the effects of sulindac sulfide on cyclic nucleotide levels in HT-29 cells.
Figure 4B:
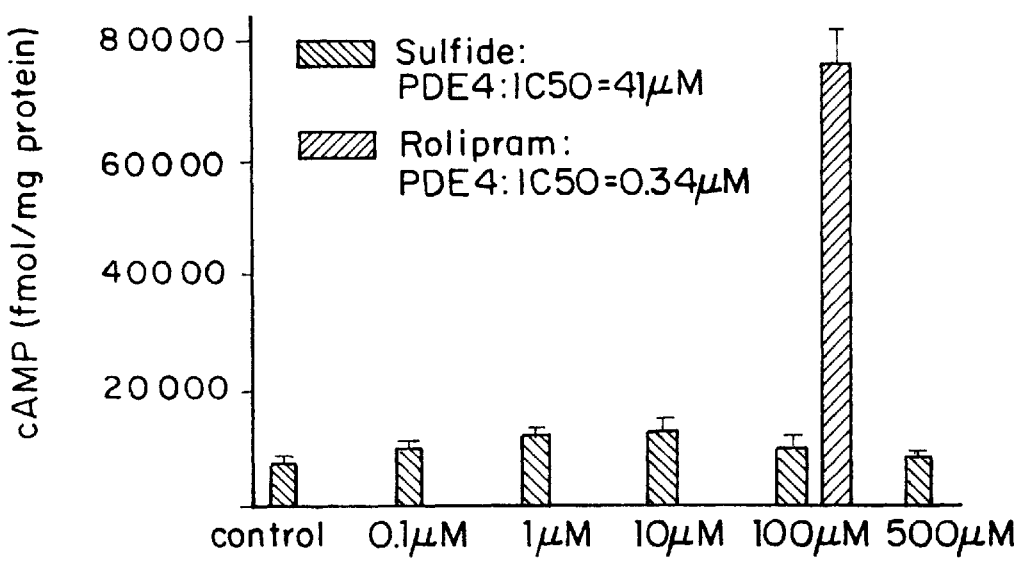

FIG. 4 shows the effects of sulindac sulfide on either cGMP or cAMP production as determined on cultured HT-29 cells in accordance with the assay of section 2.B., supra. HT-29 cells were treated with sulindac sulfide for 30 minutes and cGMP or cAMP was measured by conventional radioimmunoassay method. As indicated, sulindac sulfide increased the levels of cGMP by greater than 50% with an $EC_{50}$ value of 7.3 µM (top). Levels of cAMP were unaffected by treatment, although a known PDE4 inhibitor, rolipram, increased cAMP (bottom). The data demonstrate the pharmacological significance of inhibiting PDE5, relative to PDE4.

Figure 5:
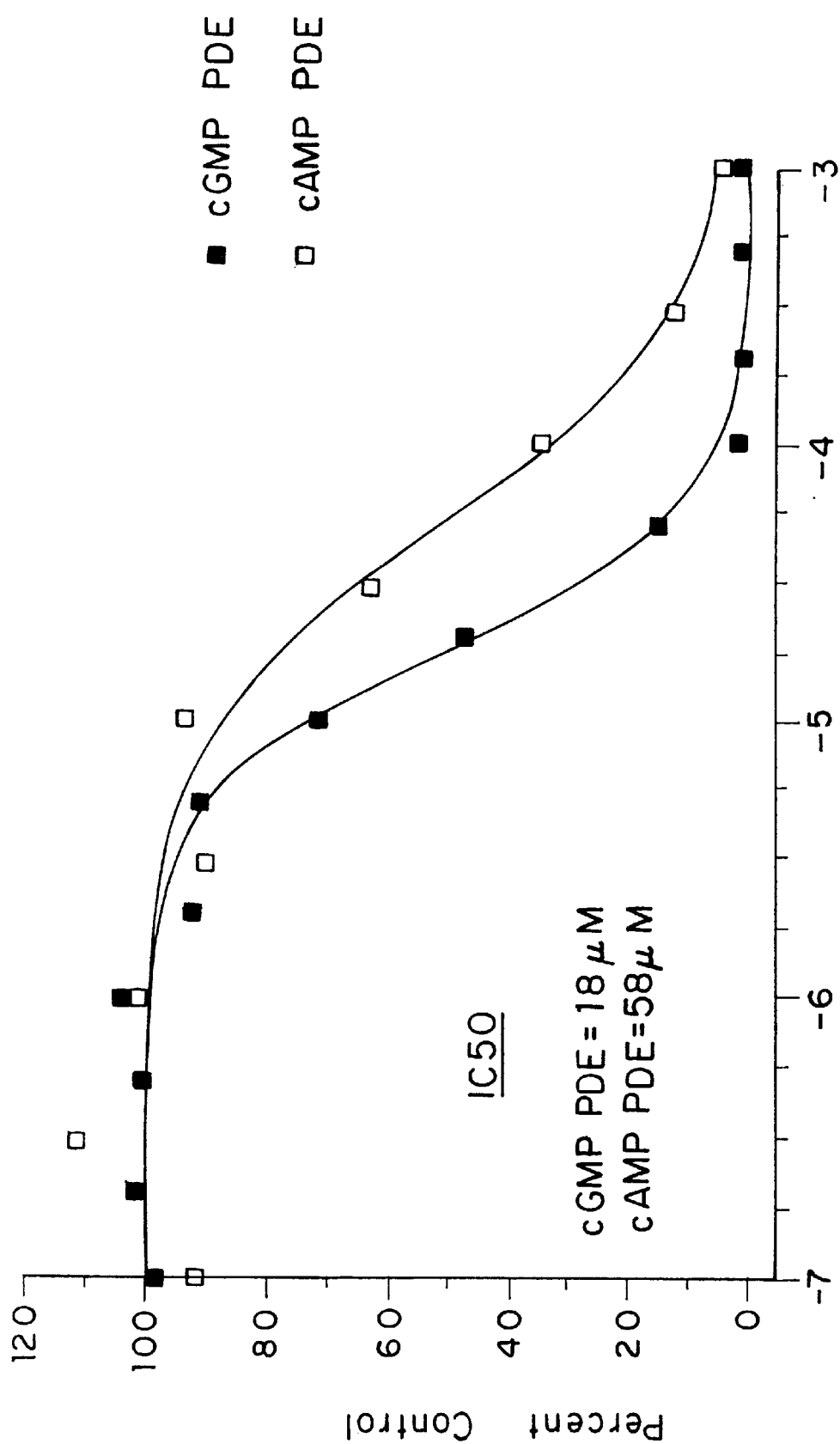
FIG. 5 illustrates the phosphodiesterase inhibitory activity of compound B.

FIG. 5 shows the effect of the indicated dose of test compound B on either PDE5 or PDE4 isozymes of phosphodiesterase. The calculated $IC_{50}$ value for PDE5 was 18 µM and 58 µM for PDE4.

Figure 6:
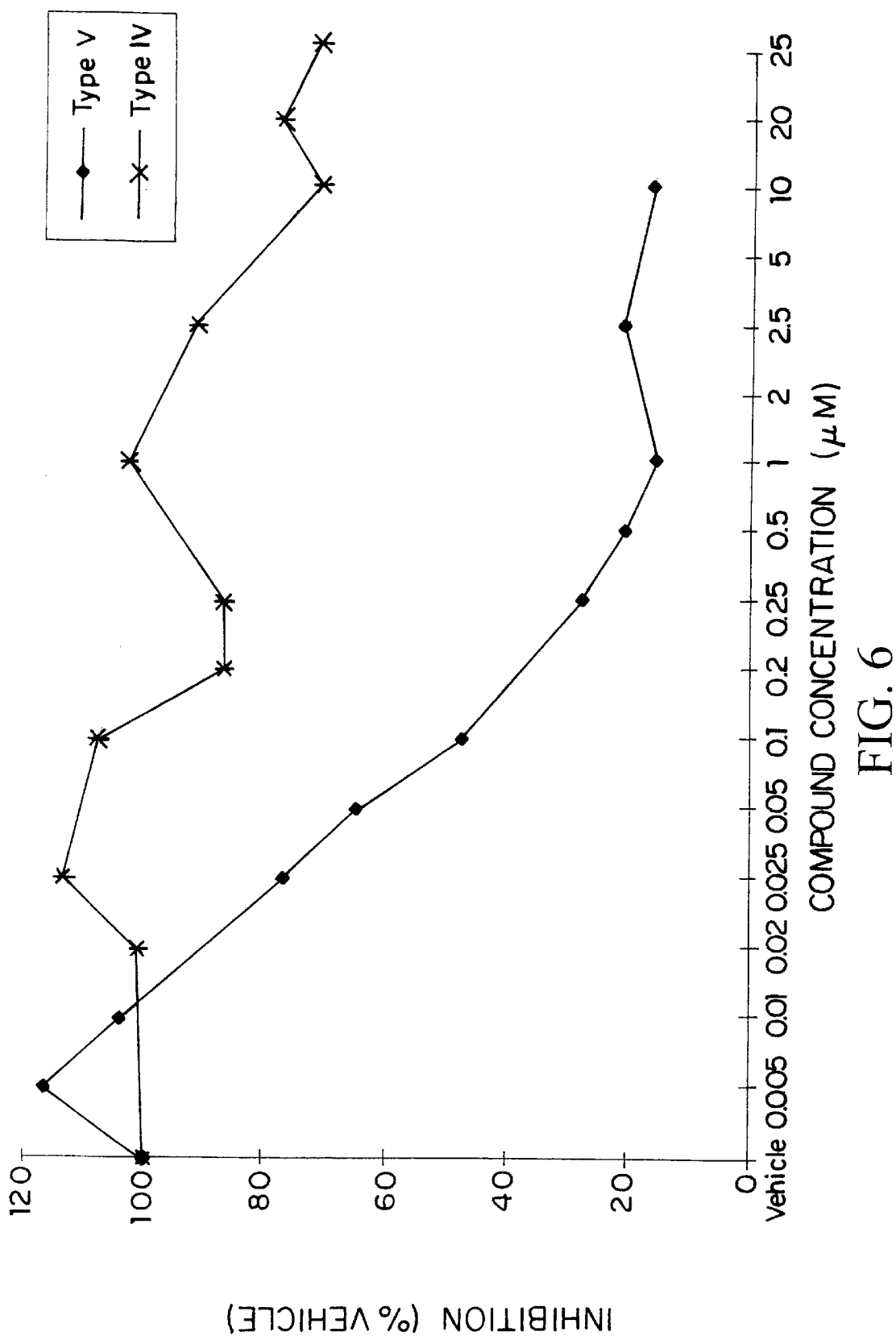
FIG. 6 illlustrates the phosphodiesterase inhibitory activity of compound E.

FIG. 6 shows the effect of the indicated dose of test compound E on either PDE4 or PDE5. The calculated $IC_{50}$ value was 0.08 µM for PDE5 and greater than 25 µM for PDE4.

TABLE 2

PDE5 inhibitory acitivity among a series of compounds

| Reference compounds | % Inhibition at 10 µM |
|---|---|
| Indomethacin | 34 |
| MY5445 | 86 |
| Sulindac sulfide | 97 |
| Exisulind | 39 |

| Test compounds | % Inhibition at 10 µM |
|---|---|
| A | <25 |
| B | <25 |
| C | <25 |

TABLE 2-continued

PDE5 inhibitory acitivity among a series of compounds

| | |
|---|---|
| D | 36 |
| E | 75 |

The above compounds in Table 2 were evaluated for PDE inhibitory activity, as described in the protocol of section 2.A; supra. Of the compounds that did not inhibit COX, only compound E was found to cause greater than 50% inhibition at 10 µM. As noted in FIG. 11, compound B showed inhibition of greater than 50% at a dose of 20 µM. Therefore, depending on the dosage level used in a single dose test, some compounds may be screened out that otherwise may be active at slightly higher dosages. The dosage used is subjective and may be lowered after active compounds are found at certain levels to identify even more potent compounds.

Example 3—Apoptosis assay

Figure 7A:
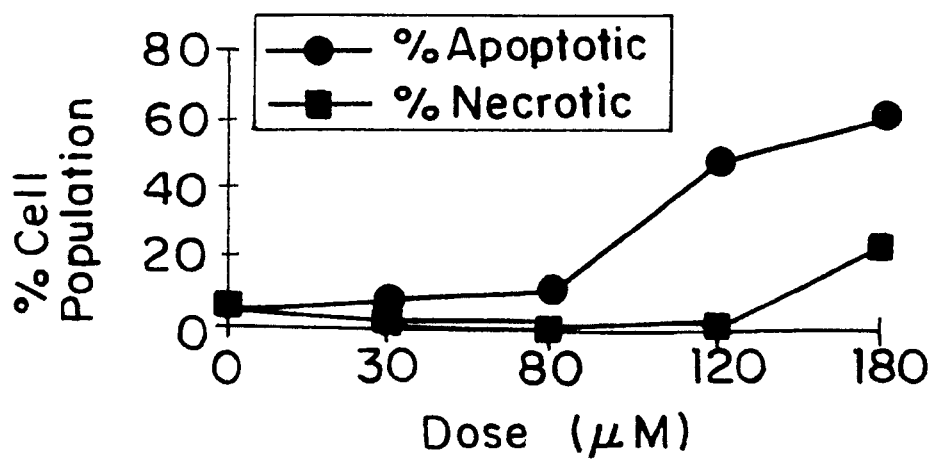
FIG. 7A illustrates the effects of sulindac sulfide on cGMP levels in HT-29 cells.
Figure 7B:
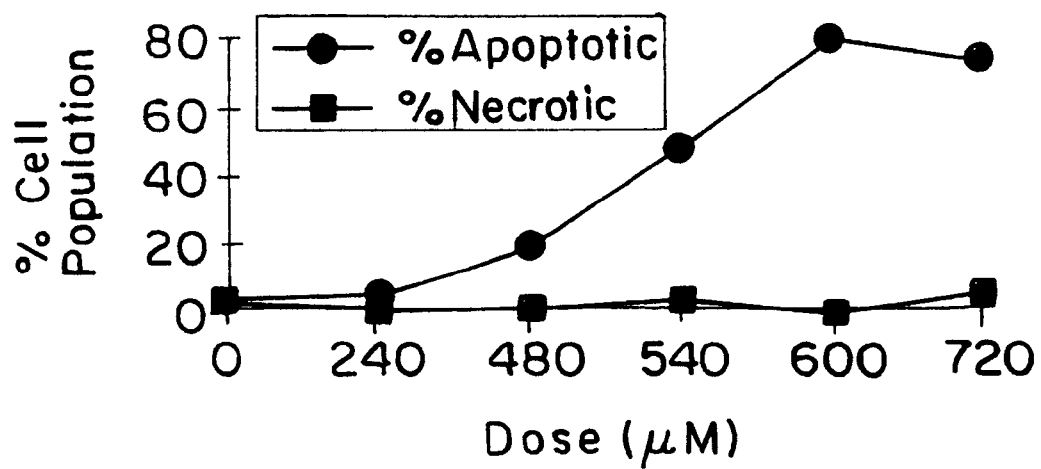
FIG. 7B illustrates the effects of sulindac sulfide on cAMP levels in HT-29 cells.

Reference compounds and test compounds were analyzed for their PDE5 inhibitory activity in accordance with the protocol for the assay of section 4.A. and 4.B., supra. In accordance with the assay of 4.A., FIG. 7 shows the effects of sulindac sulfide and exisulind on apoptotic and necrotic cell death. HT-29 cells were treated for six days with the indicated dose of either sulindac sulfide or exisulind. Apoptotic and necrotic cell death was determined previously (Duke and Cohen, In: Current Protocols in Immunology, 3.17.1–3.17.16, New York, John Wiley and Sons, 1992). The data shows that both sulindac sulfide and exisulind are capable of causing apoptotic cell death without inducing necrosis. All data were collected from the same experiment.

Figure 8A:
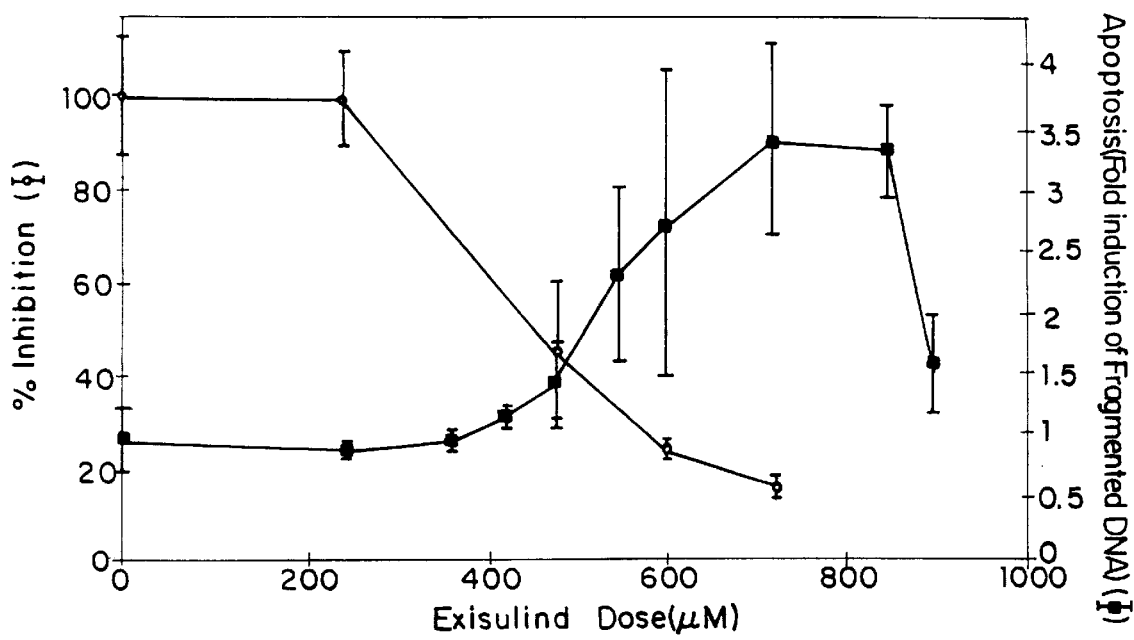
FIG. 8 illustrates the effects of sulindac sulfide and exisulind on HT-29 cell growth inhibition and apoptosis induction as determined by DNA fragmentation.
Figure 8B:
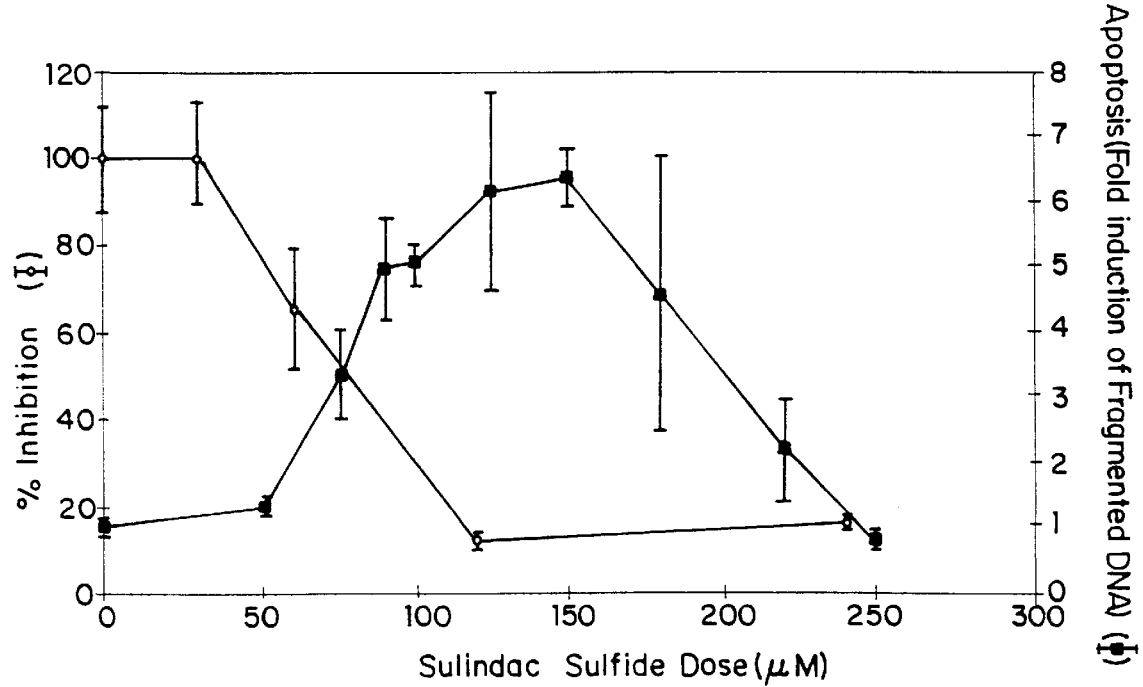

In accordance with the assay of 4.B., FIG. 8 shows the effect of sulindac sulfide and sulfone on tumor growth inhibition and apoptosis induction as determined by DNA fragmentation. Top figure; growth inhibition (open symbols, right axis) and DNA fragmentation (closed symbols, left axis) by exisulind. Bottom figure; growth inhibition (open symbols) and DNA fragmentation (closed symbols) by sulindac sulfide. Growth inhibition was determined by the SRB assay after six days of treatment. DNA fragmentation was determined after 48 hours of treatment. All data was collected from the same experiment.

Figure 9:
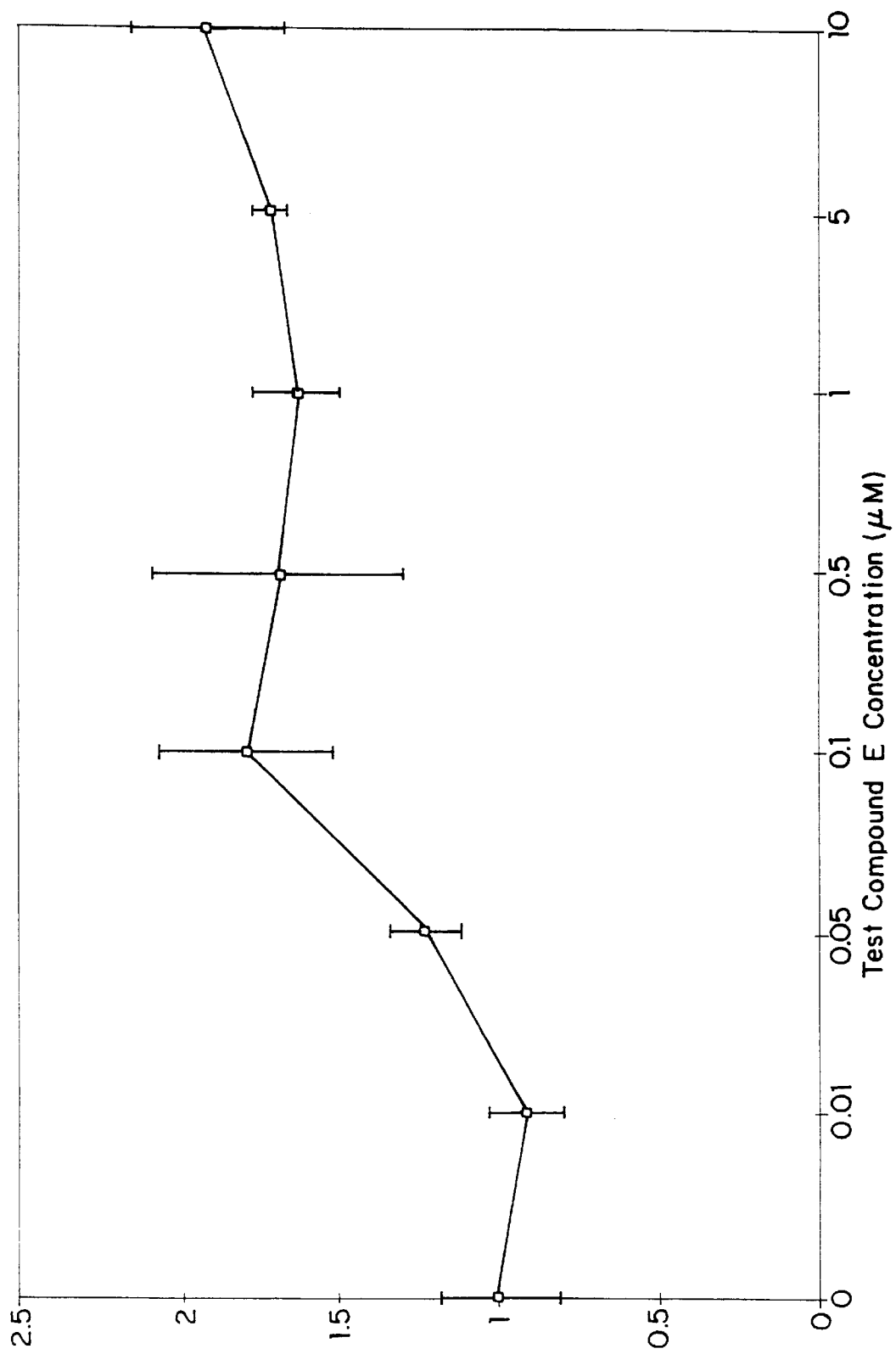
FIG. 9 illustrates the apoptosis inducing properties of compound E.

FIG. 9 shows the apoptosis inducing properties of compound E. HT-29 colon adenocarcinoma cells were treated with the indicated concentration of compound E for 48 hours and apoptosis was determined by the DNA fragmentation assay. The calculated $EC_{50}$ value was 0.05 µM.

Figure 10:
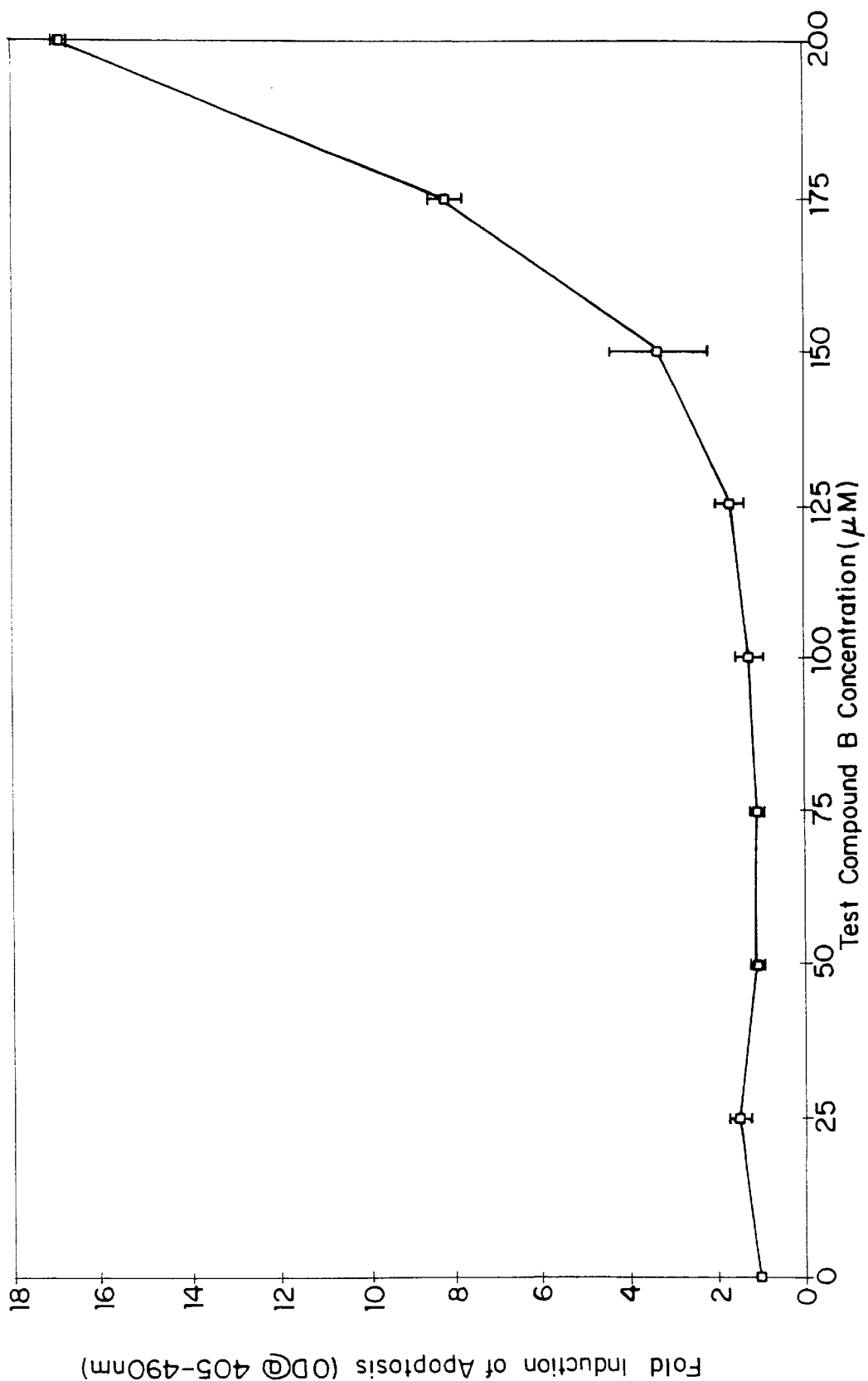
FIG. 10 illustrates the apoptosis inducing properties of compound B.

FIG. 10 shows the apoptosis inducing properties of compound B. HT-29 colon adenocarcinoma cells were treated with the indicated concentration of compound B for 48 hours and apoptosis was determined by the DNA fragmentation assay. The calculated $EC_{50}$ value was approximately 175 µM.

TABLE 3

Apoptosis inducing activity among a series of compounds

| Reference compounds | Fold induction 100 µM |
|---|---|
| Indomethacin | <2.0 |
| MY5445 | 4.7 |
| Sulindac sulfide | 7.9 |
| Exisulind | <2.0 |

| Test compounds | Fold induction at 100 µM |
|---|---|

TABLE 3-continued

Apoptosis inducing activity among a series of compounds

| | |
|---|---|
| A | <2.0 |
| B | 3.4 |
| C | 5.6 |
| D | <2.0 |
| E | 4.6 |

In accordance with the protocol of section 4.B., supra, the compounds A through E were tested for apoptosis inducing activity, as reported in Table 3 above. Compounds B, C and E showed significant apoptotic inducing activity, greater than 2.0 fold, at a dosage of 100 $\mu$M. Of these three compounds, at this dosage only B and E did not inhibit COX and inhibited PDE5.

The apoptosis inducing activity for a series of phosphodiesterase inhibitors was determined. The data are shown in Table 4 below. HT-29 cell were treated for 6 days with various inhibitors of phospohodiesterase. Apoptosis and necrosis were determined morphologically after acridine orange and ethidium bromide labelling in accordance with the assay of section 4.A., supra. The data show that PDE5 is useful for screening compounds that induce apoptosis of HT-29 cells.

TABLE 4

Apoptosis Inducing Data for PDE Inhibitors

| Inhibitor | Reported Selectivity | % Apoptosis | % Necrosis |
|---|---|---|---|
| Vehicle | | 8 | 6 |
| 8-methoxy-IBMX | PDE1 | 2 | 1 |
| Milrinone | PDE3 | 18 | 0 |
| RO-20-1724 | PDE4 | 11 | 2 |
| MY5445 | PDE5 | 80 | 5 |
| IBMX | Non-selective | 4 | 13 |

Example 4—Growth inhibition assay

Figure 11:
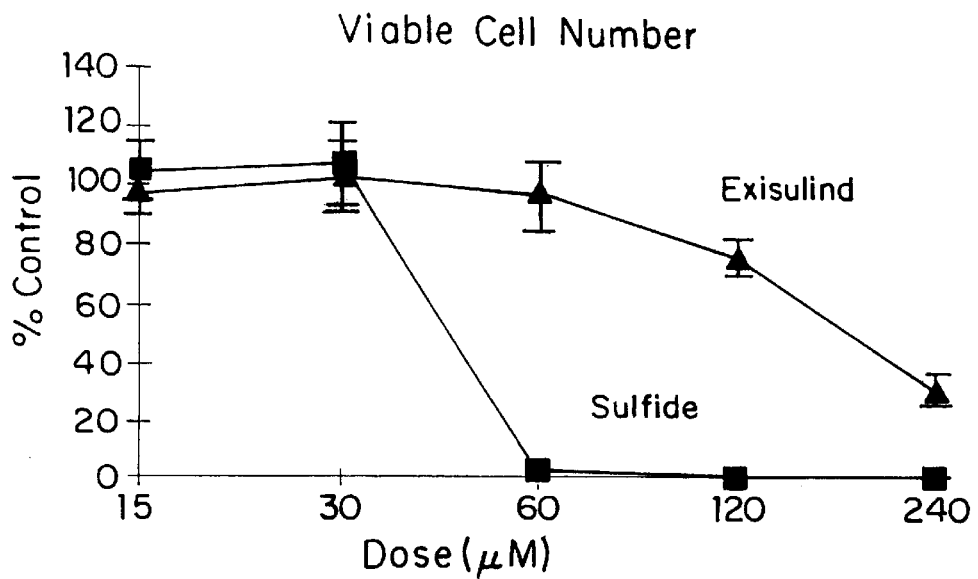
FIG. 11 illustrates the effects of sulindac sulfide and exisulind on tumor cell growth.

Reference compounds and test compounds were analyzed for their PDE5 inhibitory activity in accordance with the protocol for the assay of section 3.A., supra. FIG. 11 shows the inhibitory effect of various concentrations of sulindac sulfide and exisulind on the growth of HT-29 cells. HT-29 cells were treated for six days with various doses of exisulind (triangles) or sulfide (squares) as indicated. Cell number was measured by a sulforhodamine assay as previously described (Piazza et al., Cancer Research, 55:3110–3116, 1995). The IC$_{50}$ value for the sulfide was approximately 45 $\mu$M and 200 $\mu$M for the sulfone. The data shows that both sulindac sulfide and exisulind are capable of inhibiting tumor cell growth.

Figure 12A:
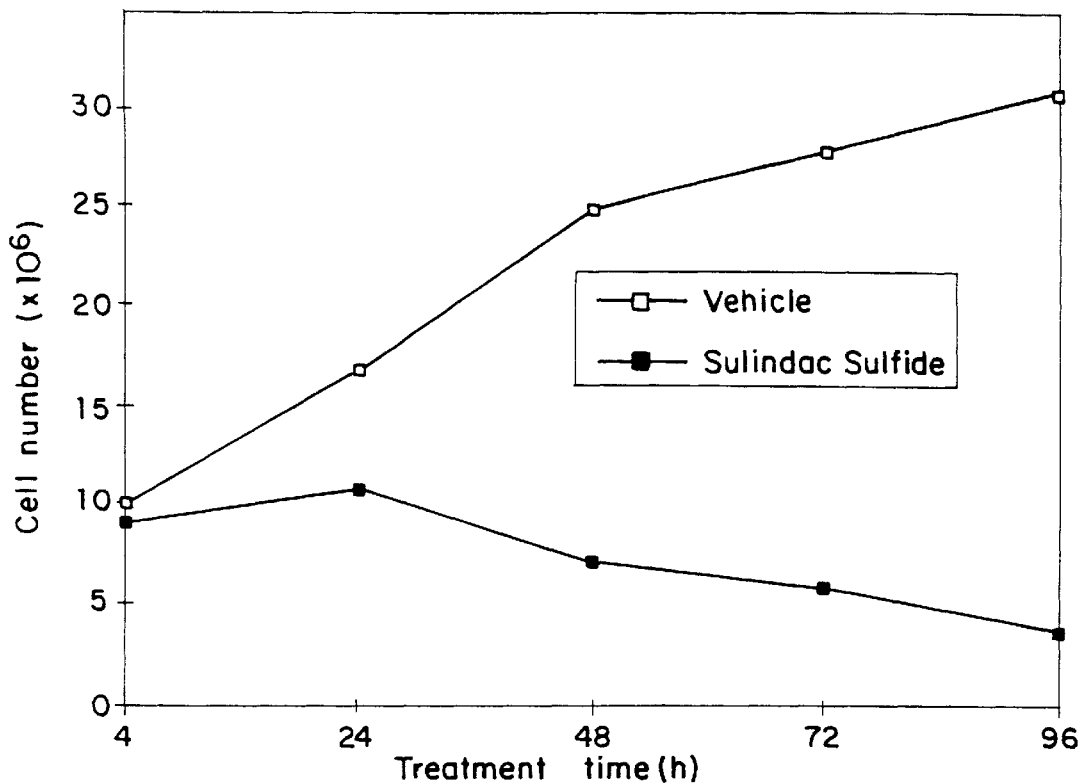
FIG. 12 illustrates the growth inhibitory and apoptosis-inducing activity of sulindac sulfide and control (DMSO).
Figure 12B:
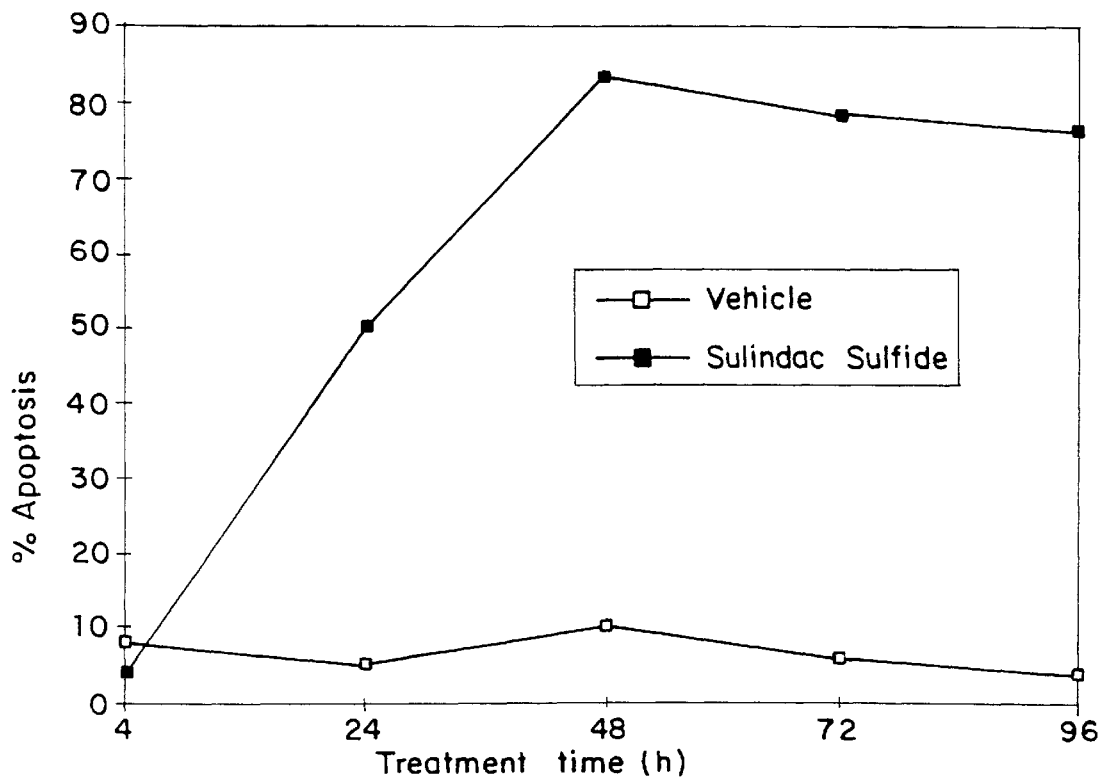

FIG. 12 shows the growth inhibitory and apoptosis-inducing activity of sulindac sulfide. A time course experiment is shown involving HT-29 cells treated with either vehicle, 0.1% DMSO (open symbols) or sulindac sulfide, 120 $\mu$M (closed symbols). Growth inhibition (top) was measured by counting viable cells after trypan blue staining. Apoptosis (bottom) was measured by morphological determination following staining with acridine orange and ethidium bromide as described previously (Duke and Cohen, In: Current Protocols in Immunology, 3.17.1–3.17.16, New York, John Wiley and Sons, 1992). The data demonstrate that sulindac sulfide is capable of inhibiting tumor cell growth and that the effect is accompanied by an increase in apoptosis. All data were collected from the same experiment.

Figure 13:
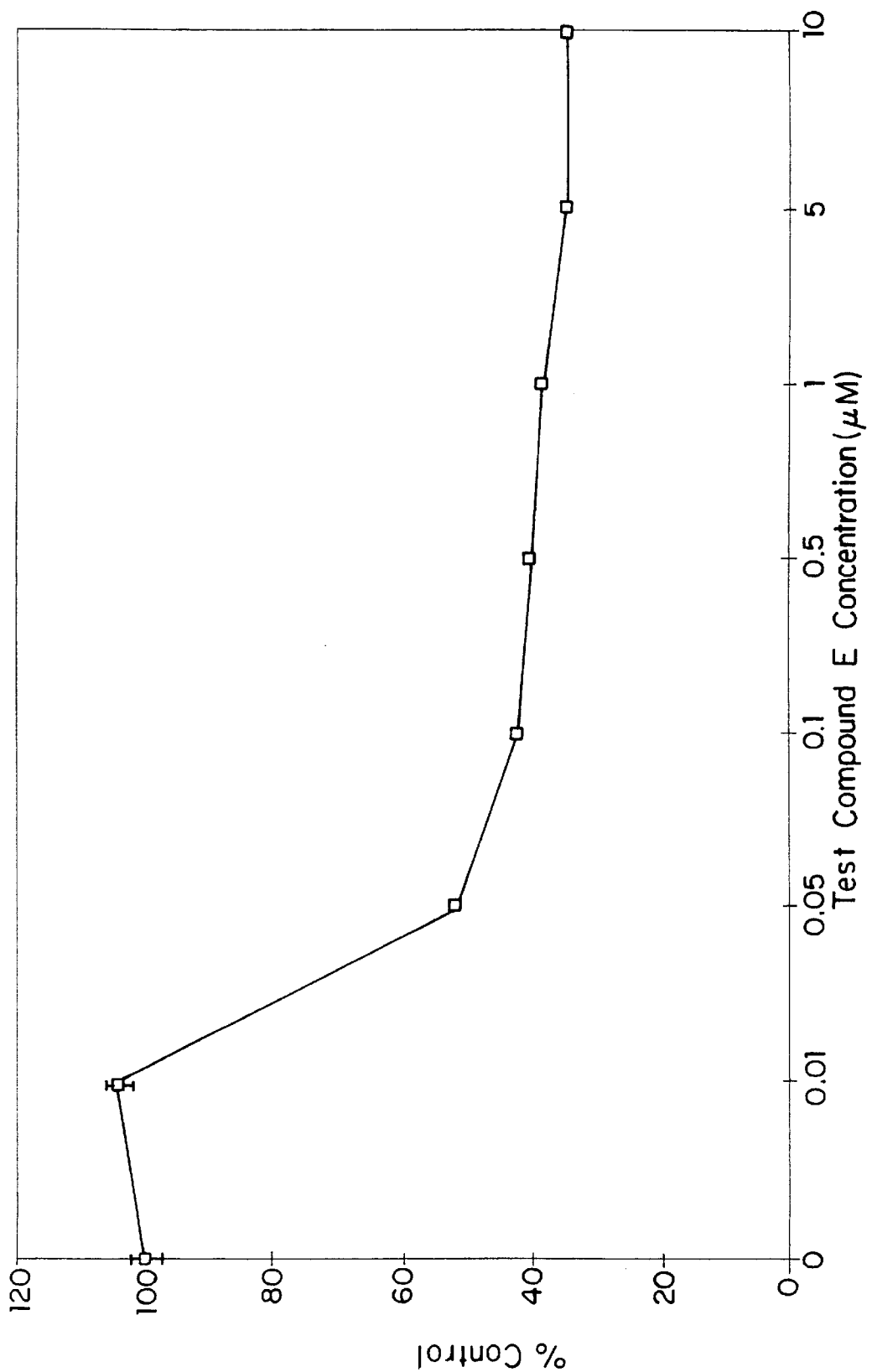
FIG. 13 illustrates the growth inhibitory activity of compound E.

FIG. 13 shows the growth inhibitory activity of test compound E. HT-29 colon adenocarcinoma cells were treated with the indicated concentration of compound E for six days and cell number was determined by the SRB assay. The calculated IC$_{50}$ value was 0.04 $\mu$M.

TABLE 5

Growth inhibitory activity among a series of compounds

| Reference compounds | % Inhibition at 100 $\mu$M |
|---|---|
| Indomethacin | 75 |
| MY5445 | 88 |
| Sulindac sulfide | 88 |
| Exisulind | <50 |

| Test compounds | % Inhibition at 100 $\mu$M |
|---|---|
| A | 68 |
| B | 77 |
| C | 80 |
| D | 78 |
| E | 62 |

In accordance with the screening protocol of section 3.A., supra, compounds A through E were tested for growth inhibitory activity, as reported in Table 5 above. All the test compounds showed activity exceeding the benchmark exisulind at a 100 $\mu$M single does test.

The growth inhibitory activity for a series of phosphodiesterase inhibitors was determined. The data are shown in Table 6 below. HT-29 cell were treated for 6 days with various inhibitors of phospohodiesterase. Cell growth was determined by the SRB assay in accordance with section 3.A., supra. The data show that inhibitors of PDE5 were effective for inhibiting tumor cell growth.

TABLE 6

Growth Inhibitory Data for PDE Inhibitors

| Inhibitor | Reported Selectivity | Growth inhibition (IC$_{50}$, $\mu$M) |
|---|---|---|
| 8-methoxy-IBMX | PDE1 | >200 $\mu$M |
| Milrinone | PDE3 | >200 $\mu$M |
| RO-20-1724 | PDE4 | >200 $\mu$M |
| MY5445 | PDE5 | 5 $\mu$M |
| IBMX | Non-selective | >100 $\mu$M |

To show the effectiveness of this screening method on various forms of neoplasia, compounds were tested on numerous cell lines. The effects of sulindac sulfide and exisulind on various cell lines was determined. The data is shown in table 7 below. The IC$_{50}$ values were determined by the SRB assay. The data shows the broad effectiveness of these compounds on a broad range of neoplasia, with effectiveness at comparable dose range. Therefore, compounds identified by this invention should be useful for treating multiple forms of neoplasia.

TABLE 7

Growth Inhibitory Data of Various Cell Lines

| Cell Type/ | IC$_{50}$($\mu$M) | |
|---|---|---|
| Tissue specificity | Sulindac sulfide | Exisulind |
| HT-29, Colon | 60 | 120 |
| HCT116, Colon | 45 | 90 |

TABLE 7-continued

Growth Inhibitory Data of Various Cell Lines

| Cell Type/ Tissue specificity | $IC_{50}(\mu M)$ | |
| --- | --- | --- |
| | Sulindac sulfide | Exisulind |
| MCF7/S, Breast | 30 | 90 |
| UACC375, Melanoma | 50 | 100 |
| A-427, Lung | 90 | 130 |
| Bronchial Epithelial Cells (normal) | 30 | 90 |
| NRK, Kidney (normal) | 50 | 180 |
| KNRK, Kidney (transformed) | 60 | 240 |
| Human Prostate Carcinoma PC3 | | 82 |

Example 5—Activity in mammary gland organ culture model

Figure 14:
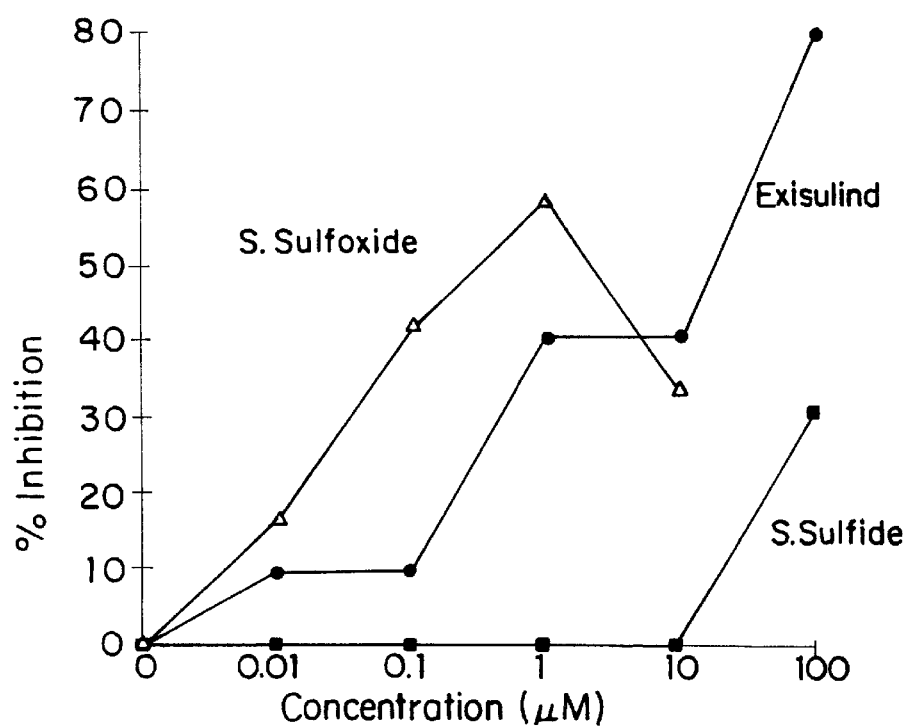
FIG. 14 illustrates the inhibition of pre-malignant, neoplastic lesions in mouse mammary gland organ culture by sulindac metabolites.

FIG. 14 shows the inhibition of premalignant lesions in mammary gland organ culture by sulindac metabolites. Mammary gland organ culture experiment were performed as previously described (Mehta and Moon, *Cancer Research*, 46: 5832–5835, 1986). The results demonstrate that sulindac and exisulind effectively inhibit the formation of premalignant lesions, while sulindac sulfide was inactive. The data support the hypothesis that cyclooxygenase inhibition is not necessary for the anti-neoplastic properties of desired compounds.

ANALYSIS

To identify compounds that have potential use for treating neoplasia, this invention provides a rationale for comparing experimental data of test compounds from several protocols. Within the framework of this invention, test compounds can be ranked according to their potential use for treating neoplasia in humans. Those compounds having desirable effects may be selected for more expensive and time consuming animal studies that are required to get approval before initiating human clinical trials.

Qualitative data of various test compounds and the several protocols are shown in Table 8 below. The data show that exisulind, compound B and compound E exhibit the appropriate activity to pass the screen of four assays: lack of COX inhibition, PDE inhibition, growth inhibition and apoptosis induction. The activity of these compounds in the mammary gland organ culture validates the effectiveness of this invention. The qualitative valuations of the screening protocols rank compound E best, then compound B and then exisulind.

TABLE 8

Activity Profile of Various Compounds

| Compound | COX In-hibition | PDE5 In-hibition | Growth In-hibition | Apoptosis | Mammary Gland Organ Culture |
| --- | --- | --- | --- | --- | --- |
| Exisulind | − | ++ | ++ | ++ | +++ |
| Sulindac sulfide | ++++ | +++ | +++ | +++ | − |
| MY5445 | ++++ | +++ | +++ | +++ | + |
| A | − | − | +++ | ++ | ++ |
| B | − | +++ | +++ | +++ | ++ |
| D | − | − | ++ | − | − |
| E | − | ++++ | ++++ | ++++ | ++++ |
| F | − | − | ++ | + | − |
| G | − | − | +++ | ++ | +++ |
| H | − | − | ++ | − | − |

Table 8 Code: Activity of compounds based on evaluating a series of experiments involving tests for maximal activity and potency.

TABLE 8-continued

Activity Profile of Various Compounds

| Compound | COX In-hibition | PDE5 In-hibition | Growth In-hibition | Apoptosis | Mammary Gland Organ Culture |
| --- | --- | --- | --- | --- | --- |

−Not active
+Slightly active
++Moderately active
+++Strongly active
++++Highest activity ever recorded Obviously, numerous modifications and variations of the present invention are possible in light of the above teachings. It is therefore to be understood that within the scope of the appended claims, the invention may be practiced otherwise than as specifically described herein.

We claim:

1. A method for identifying a compound with potential for treating neoplasia, comprising determining cyclooxygenase (COX) inhibitory activity of the compound; and determining cGMP-specific phosphodiesterase ("PDE") inhibition activity of the compound against cGMP-specific PDE enzymatic activity from adenocarcinoma cells;

wherein low COX inhibitory activity and high inhibition of said cGMP-PDE activity identifies that the compound has potential for treating neoplasia.

2. The method of claim 1, further comprising determining whether the compound inhibits tumor cell growth in a culture;

wherein inhibition of tumor cell growth further identifies that the compound has potential for treating neoplasia.

3. The method of claim 1, further comprising determining whether the compound induces apoptosis of a tumor cell;

wherein induction of apoptosis further identifies that the compound has potential for treating neoplasia.

4. The method of claim 3, further comprising determining whether the compound inhibits tumor cell growth in a sample;

wherein inhibition of tumor cell growth further indicates that the compound has potential for treating neoplasia.

5. A method of selecting a compound potentially useful for treating of neoplasia, comprising determining neoplastic cell growth inhibitory activity of the compound;

determining cGMP-specific PDE inhibition activity of the compound against cGMP-specific PDE enzymatic activity from adenocarcinoma cells; and selecting a compound that exhibits growth inhibitory activity and said cGMP-specific enzyme inhibitory activity.

6. The method of claim 5, further comprising determining whether the compound induces apoptosis in a cell; and selecting a compound that induce apoptosis.

7. The method of claim 6, further comprising:

determining the COX inhibitory activity of the compound; and selecting a compound with low COX inhibitory activity relative to said PDE-inhibitory activity.

8. The method of claim 7, wherein the COX inhibitory activity of the compound is determined by:
contacting the compound with a cyclooxygenase; and
measuring the change, if any, of cyclooxygenase activity;
wherein a decrease in cyclooxygenase activity correlates to a decrease in prostaglandin synthetase activity.

9. The method of claims 7, wherein the COX inhibitory activity of the compound is determined by:
contacting the compound with a cell which secretes PGE-2; and
measuring the decrease, if any, of the PGE-2 secretion from the cell;
wherein a decrease in PGE-2 secretion correlates to a decrease in prostaglandin synthetase activity.

10. A method for identifying a compound potentially useful for administering to patients in need of treatment for neoplasia, comprising the steps of:
determining the COX inhibitory activity of the compound;
determining the cGMP-specific PDE inhibition activity of the compound; and
identifying those compounds for potential use in treating neoplasia in patients in need thereof if the compounds exhibit PDE inhibition activity and have COX inhibitory activity lower that said PDE inhibition activity.

11. The method of claim 10 further comprising determining the growth inhibitory activity of the compounds; and identifying those compounds with phosphodiesterase inhibitory activity substantially greater than COX inhibitory activity at concentrations exhibiting substantial growth inhibitory activity.

12. The method of claim 11 wherein the growth inhibitory activity is determined by the reduction of the number of cells in a sample.

13. The method of claim 11 wherein the growth inhibitory activity is determined by inducing apoptosis in a sample.

14. A method for identifying a compound with potential for treating neoplasia, comprising:
selecting a compound with cGMP-specific PDE inhibiting activity
evaluating neoplastic cell growth inhibiting activity of the compound; and
identifying the compound that exhibits cGMP-specific PDE inhibiting activity and neoplastic cell growth inhibiting activity wherein said compound has the potential to inhibit neoplasia without substantially inhibiting the growth of normal cells.

* * * * *